(12) United States Patent
Oostman, Jr.

(10) Patent No.: US 9,510,913 B2
(45) Date of Patent: Dec. 6, 2016

(54) SKIN TENSIONING DEVICES AND METHODS OF THEIR USE

(71) Applicant: Restoration Robotics, Inc., San Jose, CA (US)

(72) Inventor: Clifford A. Oostman, Jr., Hansville, WA (US)

(73) Assignee: Restoration Robotics, Inc., San Jose, CA (US)

( * ) Notice: Subject to any disclaimer, the term of this patent is extended or adjusted under 35 U.S.C. 154(b) by 752 days.

(21) Appl. No.: 13/787,586

(22) Filed: Mar. 6, 2013

(65) Prior Publication Data

US 2014/0074115 A1    Mar. 13, 2014

Related U.S. Application Data

(60) Provisional application No. 61/700,233, filed on Sep. 12, 2012.

(51) Int. Cl.
*A61B 90/00* (2016.01)
*A61B 19/00* (2006.01)

(52) U.S. Cl.
CPC .............. *A61B 19/24* (2013.01); *A61B 90/02* (2016.02); *A61B 34/30* (2016.02)

(58) Field of Classification Search
CPC .............. A61B 2017/00752; A61B 17/32093; A61B 17/322; A61B 2017/3225; A61B 19/24; A61B 19/26; A61B 19/22; A61B 19/2203; A61F 2/12; A61F 2/105; A61F 2/10

See application file for complete search history.

(56) References Cited

U.S. PATENT DOCUMENTS

| 1,550,403 A | 8/1925 | Turkus |
| 4,370,979 A | 2/1983 | Erickson |
| 4,434,791 A | 3/1984 | Darnell |

(Continued)

FOREIGN PATENT DOCUMENTS

| DE | 44 44 130 A1 | 6/1995 |
| WO | 0103588 A1 | 1/2001 |

(Continued)

OTHER PUBLICATIONS

PCT Search Report and Written Opinion mailed Nov. 12, 2013, in connection with commonly assigned PCT Application No. PCT/2013/056130, Forms PCT/ISA/220, PCT/ISA/210 and PCT/ISA/237, Nov. 12, 2013, (13 pages).

(Continued)

*Primary Examiner* — Tuan V Nguyen
*Assistant Examiner* — Chima Igboko
(74) *Attorney, Agent, or Firm* — Sharon Upham; Lena I. Vinitskaya

(57) ABSTRACT

Devices and methods for applying tension to an area of skin during various cosmetic or dermatological procedures, in particular for follicular unit removal and/or implantation in a hair transplantation procedure, are provided. The systems and methods utilize a segmented structure configured to conform to the body surface of various sizes, shapes and/or textures, thus allowing for customization in order to fit a variety of persons. In some embodiments, the tensioning device may be temporary secured, for example, to a patient chair.

35 Claims, 13 Drawing Sheets

(56) References Cited

U.S. PATENT DOCUMENTS

| | | |
|---|---|---|
| 4,621,619 A | 11/1986 | Sharpe |
| 4,896,680 A | 1/1990 | Hirshowitz |
| 5,089,009 A | 2/1992 | Green |
| 5,441,540 A | 8/1995 | Kim |
| 5,449,374 A | 9/1995 | Dunn et al. |
| 5,486,196 A | 1/1996 | Hirshowitz et al. |
| 5,531,790 A | 7/1996 | Frechet et al. |
| 5,662,714 A | 9/1997 | Charvin et al. |
| 5,759,193 A | 6/1998 | Burbank et al. |
| 5,769,783 A | 6/1998 | Fowler |
| 5,785,649 A | 7/1998 | Fowler, Jr. |
| 5,814,067 A | 9/1998 | Fleischmann |
| 5,931,777 A | 8/1999 | Sava |
| 5,964,697 A | 10/1999 | Fowler, Jr. |
| 5,971,920 A | 10/1999 | Nagel |
| 5,972,021 A | 10/1999 | Huttner et al. |
| 6,036,641 A | 3/2000 | Taylor et al. |
| 6,120,436 A | 9/2000 | Anderson et al. |
| 6,159,231 A | 12/2000 | Looney et al. |
| 6,190,312 B1 | 2/2001 | Fowler, Jr. |
| 6,254,624 B1 | 7/2001 | Oddsen et al. |
| 6,464,634 B1 | 10/2002 | Fraser |
| 6,695,868 B2 | 2/2004 | Looney et al. |
| 7,208,006 B2 | 4/2007 | Fleischmann |
| 2002/0087051 A1 | 7/2002 | Levisman |
| 2003/0120298 A1 | 6/2003 | Gildenberg |
| 2004/0049206 A1* | 3/2004 | Rassman ............ A61B 19/24 606/133 |
| 2006/0270909 A1 | 11/2006 | Davis |
| 2007/0021779 A1 | 1/2007 | Garvin et al. |
| 2007/0049970 A1 | 3/2007 | Belef et al. |
| 2007/0078466 A1* | 4/2007 | Bodduluri ........ A61B 17/32053 606/133 |
| 2007/0282374 A1 | 12/2007 | Sogard et al. |
| 2008/0027484 A1 | 1/2008 | Lee et al. |
| 2008/0114395 A1 | 5/2008 | Mathisen et al. |
| 2010/0030260 A1 | 2/2010 | Fleischmann |
| 2010/0191253 A1* | 7/2010 | Oostman, Jr. ...... A61B 17/0206 606/133 |
| 2011/0152627 A1 | 6/2011 | Tannoury et al. |
| 2011/0178533 A1* | 7/2011 | Oostman, Jr. ........... A61B 19/24 606/133 |
| 2012/0041451 A1* | 2/2012 | Bodduluri ........ A61B 17/32053 606/133 |

FOREIGN PATENT DOCUMENTS

| | | |
|---|---|---|
| WO | 2006132256 A1 | 12/2006 |
| WO | 2008/107110 | 9/2008 |
| WO | 2011064772 | 6/2011 |

OTHER PUBLICATIONS

PCT International Search Report in relation to commonly assigned PCT application, PCT/US2010/021353, Applicant: Restoration Robotics, Inc., Forms PCT/ISA/210, 220 and 237, dated Jun. 29, 2010 (20 pages).

* cited by examiner

SKIN TENSIONING DEVICES AND METHODS OF THEIR USE

RELATED APPLICATIONS

This application claims priority under 35 U.S.C. 119(e) to U.S. Provisional Application No. 61/700,233 filed Sep. 12, 2012, entitled "Skin Tensioning Devices and Methods of Their Use".

FIELD OF THE INVENTION

The present invention relates generally to devices, systems and methods for applying tension to an area of a body surface and, in particular, skin tensioners and methods of their use in conjunction with hair transplantation procedures.

BACKGROUND OF THE INVENTION

There are numerous surgical, cosmetic, therapeutic and dermatological procedures that involve maneuvering an area of skin and it is often beneficial to create tension in a skin area or a body surface where a particular procedure is performed. By way of example, hair transplantation is one of those procedures and it typically involves harvesting donor hair grafts from the "donor areas," for example, side and back fringe areas of the patient's scalp, or other body surfaces, and implanting them in a bald area ("recipient area"). Hair transplantation is a very labor-intensive and complex procedure that requires skill and precision. Various techniques were developed over the years for harvesting donor hair grafts. One such technique involves excising a strip of skin from the back area of the scalp and then dissecting the strip under a microscope to isolate individual hair follicular units for later implantation into the recipient area. This technique suffers numerous disadvantages, including being very time consuming, tedious, expensive, and requiring suturing and resulting scarring. Another technique called Follicular Unit Extraction ("FUE") allows harvest of individual follicular units without a need to cut a strip of tissue from the patient's scalp.

An FUE method for harvesting follicular units allows for individual follicular units to be harvested directly from the donor area by utilizing a hollow punch having a cutting edge and an interior lumen with a diameter of, for example, 1 mm. The punch is used to make a small circular incision in the skin around the follicular unit. Thereafter, the follicular unit is removed, e.g., using forceps, for subsequent implantation into a recipient site with a specially devised insertion needle. FUE procedure avoids scarring associated with cutting a strip of scalp, reduces patient's discomfort, and reduces recovery time, however, it is a laborious procedure, take a long time to perform and it requires a high degree of technical skill. During such procedures, typically manually performed by a physician, in order to tension a skin surface in the area of hair harvesting or implantation, pressure is typically applied adjacent the target location using two fingers. Similar skin tensioning techniques are used in various cosmetic and dermatological procedures other than hair transplantation.

One automated system for harvesting follicular units from a body surface is disclosed in U.S. Patent Publication 2007/0078466. In one embodiment a skin tensioner in the form of two tines presses against a skin surface to thereby tension the skin. Another example of a skin tensioner is described in commonly assigned U.S. Patent Publication Number US2010/0191253.

SUMMARY

The present application provides various skin tensioning devices and methods of their use that have different unique features that are especially useful in various cosmetic and dermatological procedures. According to one aspect, a skin tensioning device forming a frame is provided. The frame comprises a pair of elongated legs spaced apart from one another and each having a length. At least a portion of the length of each leg extends generally parallel to the other, wherein a generally rectangular opening is defined between the parallel portions of the legs which has a height dimension approximately equal to the spacing between the legs and a length dimension approximately equal to the length of the parallel portions of the legs. Furthermore, each leg of the pair of the legs comprises at least two segments connected in series by a joint that is more flexible than the segments. A plurality of body surface grabbers is provided along each segment of at least one of the legs, the body surface grabbers being configured to apply a grabbing force to the body surface. The frame is configured to 1) conform to a curved body surface by adjusting a relative position and/or curvature of the at least two segments and 2) apply tension to the body surface by adjusting the height of the opening or by a force directed to at least one of the segments of the leg that has the body surface grabbers and away from the other leg.

In one embodiment, the segments are substantially rigid, while in other embodiments they may be flexible. Preferably, the segments and the flexible joint comprise the same material, but in some embodiments may comprise different materials. The segments and their joints may form an integrated unit, for example, a unitary molded polymer member. In one version of the frame, the segments comprise different lengths. For instance, the elongated leg comprises at least three segments, two end segments and a middle segment, wherein the segments are attached end-to-end, and wherein the end segments may be shorter in length than the middle segment. The segments may be detachable from each other, and the frame configured to allow adjustment of a number of the segments. The number of segments in the elongate member may comprise a number to substantially span the body surface. The exemplary frame may also have visual fiducials on the frame, for example, on an upper surface of each segment. The elongated legs may be configured to conform to the body surface. In certain embodiments, the opening of the frame of skin tensioner is long and narrow such that the height of the opening is approximately 10-40% of the length of the opening. In some embodiments, the skin tensioning device further includes at least two securing members attached to the frame and configured such that in operation they securely anchor the frame to the body surface. In other embodiments, the skin tensioning device may contain relatively rigid segments so that the device may conform to the body surface without creating substantial tension in the skin, and it further includes a plurality of securing members attached to the frame and configured such that in operation such securing members can be adjusted to create or further alter a tension applied to the body surface. For example, the securing members may each comprise a flexible strand. In one embodiment there may be a plurality of body surface grabbers provided along each segment of each of the legs.

Another aspect of the present invention is a multi-segment frame configured to conform to a body surface and apply tension thereto. The frame includes a plurality of segments extending in series in at least one direction, and defines a perimeter and an opening in the frame. At least one of the plurality of segments is configured to move relative to an adjacent one of the plurality of segments, such that the frame can be configured to conform to the body surface. Further, each of the segments comprises at least one body surface grabber. Finally, a support member attaches to and securely anchors the frame to the body surface.

In accordance with yet another aspect, a tensioner is configured to conform to a body surface and apply tension thereto and comprises two laterally spaced elongated legs, coupled to each other at their respective ends thereof to define a continuous boundary and an opening therein. Each elongated leg comprises a plurality of segments and has at least one body surface grabber, wherein at least one of the plurality of segments is configured to move relative to an adjacent one of the plurality of segments, such that the elongated member conforms to the body surface. At least two anchoring locations are disposed on the tensioner, each anchoring location accommodating a securing member, wherein anchoring of one end of the securing member to the tensioner and the other end to a fixed point other than the frame provides for secure attachment of the tensioner to the body surface. The securing member preferably comprises a flexible strand, which may be adjustably tightened to alter a tension applied to the body surface by the tensioner. In a preferred embodiment the flexible strand is detachable from the tensioner. Also, each segment preferably has at least one body surface grabber, and the body surface grabber may be one or more of a barb or a microbarb.

In some embodiments the elongated legs may be directly coupled. The plurality of segments are preferably coupled by a flexible joint permitting flexing of the elongated leg. In one embodiment the segments and the flexible interconnections comprise the same material such as being molded as a single unit. In another, the flexible joint comprises a hinge or pivot, which may be lockable. The segments may vary in shape and be of different lengths. A unique characteristic such as color may be used to identify each length. The elongated leg may comprise a plurality of segments coupled end-to-end. The number of segments in the elongated leg may be selected such that the elongated leg substantially spans the desired body surface, for instance the rear of a patient's scalp. The anchoring location may comprise an aperture in an elongated leg, or a channel running through the leg through which a strand may be passed.

The present application is also directed to methods for performing procedures on a body surface utilizing skin tensioners of the present application. According to certain embodiments, one such method comprises positioning a skin tensioner having a frame over a first region on the body surface where a first procedure is to be performed, the positioning is such that an elongated opening defined by the frame is over at least a portion of the first region; performing the first procedure in the first region and within the elongated opening; positioning the skin tensioner on the body surface over a second region where a second procedure is to be performed such that the elongated opening is over at least a portion of the second region and such that an intermediate region comprising hair follicles is disposed between the first and second regions; directing the hair follicles in the intermediate region in a direction away from the second region; performing a second procedure in the second region and within the elongated opening; and covering at least a portion of one of the first or second regions where the procedure was performed with hair follicles from the intermediate region.

"Performing the procedure" step of the above method includes, without limitation, not only manual performance of the procedure but also initiating, overseeing or directing any levels of automated performance of the procedure, for example, by directing or overseeing operation of a partially or fully automated device, or computer-assisted device, such as a robotic device. The method of performing a procedure may include directing hair follicles positioned adjacent the first and/or second region, away from the respective first and/or second region, prior to performing the procedure in the respective first and/or second region. The method may further include shaving or cutting at least some hair follicles in the first and/or second regions prior to or after positioning the skin tensioner over the respective first and/or second region. In one embodiment, the method further comprises conforming the skin tensioner to the curvature of the first and/or second region. In another embodiment, one or more securing members are used to create or adjust tension applied to the frame of the skin tensioner to the body surface. The method may include fastening a second end of a securing member, whose first end is attached to the frame, to a fixed location other than the frame, to provide secure attachment of the frame to the body surface. The method may further include adjusting the securing member to adjust the tension applied by the frame to the body surface. The procedure on a body surface may include, for example, hair harvesting, hair implantation, or any other cosmetic or dermatological procedure where it is desirable to create skin tension. Further examples include, but are not limited to, biopsy procedures, tattoo procedures, or procedures requiring the injection of substances into the skin and/or muscles at precise levels or in precise amounts (for example, various fillers, pharmaceutical agents, cells etc.)

According to further embodiments, another method for performing a procedure on a body surface utilizing a skin tensioner is provided. The method comprises selecting a first region where a first procedure is to be performed; positioning on the body surface a skin tensioner having a frame such that an elongated opening defined by the frame is over at least a portion of the first region; and operating or directing operation of a tool to perform the first procedure in the first region and within the elongated opening. The method further comprises selecting a second region where a second procedure is to be performed such that an intermediate region comprising hair follicles is disposed between the first and second regions; directing the hair follicles in the intermediate region in a direction away from the second region; and positioning the skin tensioner on the body surface such that the elongated opening is over at least a portion of the second region. The second procedure is performed by operating or directing operation of the same or a different tool in the second region and within the elongated opening. Finally, the method comprises covering at least a portion of one of the first or second regions where the procedure was performed with hair follicles from the intermediate region.

Other and further objects, advantages and embodiments of the inventions of the present application will become apparent from the following detailed description when read in view of the accompanying figures.

BRIEF DESCRIPTION OF THE DRAWINGS

Features and advantages of the embodiments described herein will become appreciated as the same become better understood with reference to the specification, claims, and appended drawings wherein:

FIG. 1b is a schematic perspective view of the underside of the elongated skin tensioning device of FIG. 1a;

FIGS. 1c and 1d are top plan and side elevational views of the elongated skin tensioning device of FIG. 1a;

FIG. 3b is a schematic perspective view of the underside of the three-segment elongated skin tensioning device of FIG. 3a;

FIGS. 3c and 3d are top plan and side elevational views of the three-segment elongated skin tensioning device of FIG. 3a;

DETAILED DESCRIPTION OF THE PREFERRED EMBODIMENTS

Figure 1A:
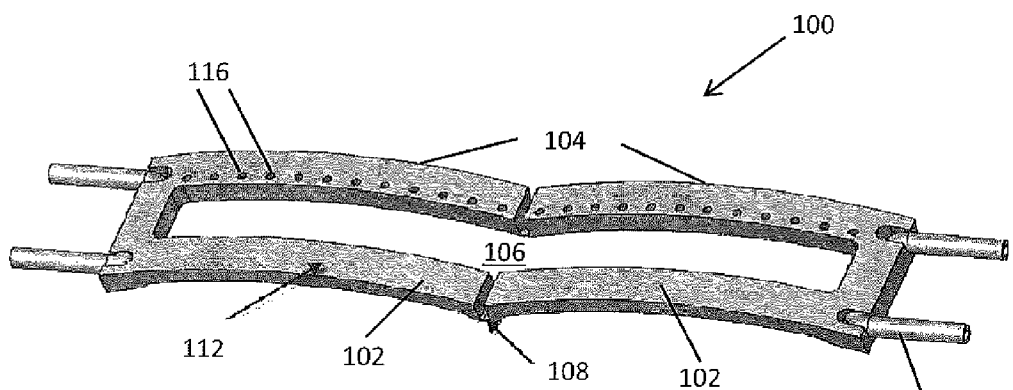
FIG. 1a is a schematic perspective view of the upper surface of an example of a two-segment elongated skin tensioning device.

In the following Detailed Description reference is made to the accompanying drawings that show by way of illustration specific embodiments in which the invention may be practiced. In this regard, directional terms, such as "upper," "underside," "lower," "upwards," "downwards," "inner," "front," "away," "above," "below," etc., are used with reference to the orientation of the Figure(s) being described. Because components or embodiments of the present invention can be positioned in a number of different orientations, and the methods can be carried out in a number of different ways, the directional terminology is used for purposes of illustration and is in no way limiting. Also, the terms "coupled," or "attached," or "connected," or "mounted" as used herein, means directly or indirectly coupled, attached, connected, integrated, or mounted, for example, through one or more intervening components. It is to be understood that other embodiments may be utilized and structural or logical changes may be made without departing from the scope of the present invention. The following Detailed Description, therefore, is not to be taken in a limiting sense, and the scope of the present invention is defined by the appended claims.

As mentioned above, though the invention is particularly useful in hair harvesting and implantation to provide devices and methods for harvesting and implanting follicular units (FUs), it is not limited to hair transplantation. Other procedures where skin or any body surface is desired to be tensioned may benefit from the system and method of the inventions described herein. One example of applicability of the invention is in diagnostic skin imaging for cosmetic or other medical purposes. Other example of procedures include but are not limited to hair harvesting, hair implantation, biopsy procedures, tattoo placement and removal procedures, or procedures requiring the injection of various substances into the skin and/or muscles, especially when precise levels or precise amounts are important (for example, Botox®, fillers, pharmaceutical agents, stem cells etc.). For convenience of description, the following description will be discussed by example in reference to hair transplantation procedures. It should be noted, however, that such description is for the purposes of illustration and example only and is not intended to be exhaustive or limiting.

Body surfaces come in various sizes, shapes and textures, and it has been found that a skin tensioning device that may work for one person, may not work in quite the same way for another person. In addition, body surfaces may have medical conditions or history associated with them, for example psoriasis, raised moles, or scars from a previous surgery or hair transplantation. According to one aspect, the present application describes devices, systems and methods of use for utilizing a skin tensioner that can conform to a body surface, and create tension across region of a body surface, to facilitate various procedures on the body surface, for example, harvesting of follicular units (FUs) from various locations on a body surface. In some embodiments, the devices, systems and methods utilize a structure configured conform to and span any region of the body surface, body surfaces of various sizes, shapes and/or textures, thus allowing for customization in order to fit a variety of body surfaces. The devices, systems and methods described herein also allow performing procedures on a region or an area comprising multiple curvatures, for example spanning from one side of a patient's head to the other. For purposes of clarity, creating tension in a skin surface means applying a tensile force such that the skin surface exhibits tension greater than any tension existing in the relaxed state. Typically, this requires pulling apart, or applying separating forces to, two spaced locations, with the area in between experiencing tension.

Figure 1B:
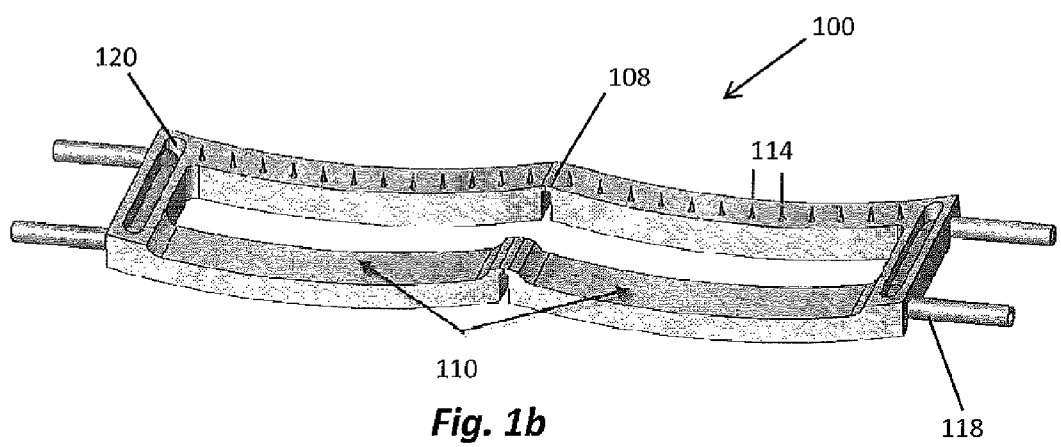

According to an aspect of the present application, a body surface tensioning device is provided that allows the user to provide tension (including substantially uniform tension) in a body surface across a treatment area of various size, shape and/or texture. FIGS. 1a and 1b illustrate perspective views of the upper surface and underside, respectively, of a two-segment body surface tensioning device 100 that can be utilized to create a body surface tensioning device that both extends across and conforms to a body surface. The tensioner 100 comprises two segments 102 that connect at their open ends to form a continuous frame 104 with a peripheral boundary defining an opening 106 therein. In this manner, a frame 104 having two elongate generally parallel legs connected by two shorter sides on each end is created. A body surface tensioner of this configuration defines an elongated opening 106, the size of which may span across a patient's head or a portion thereof, for example. The segments 102 may be of any size, thereby allowing for smaller segments to be used when the patient has a smaller sized head, and for larger segments to be used for those with a larger sized head.

Figure 1C:
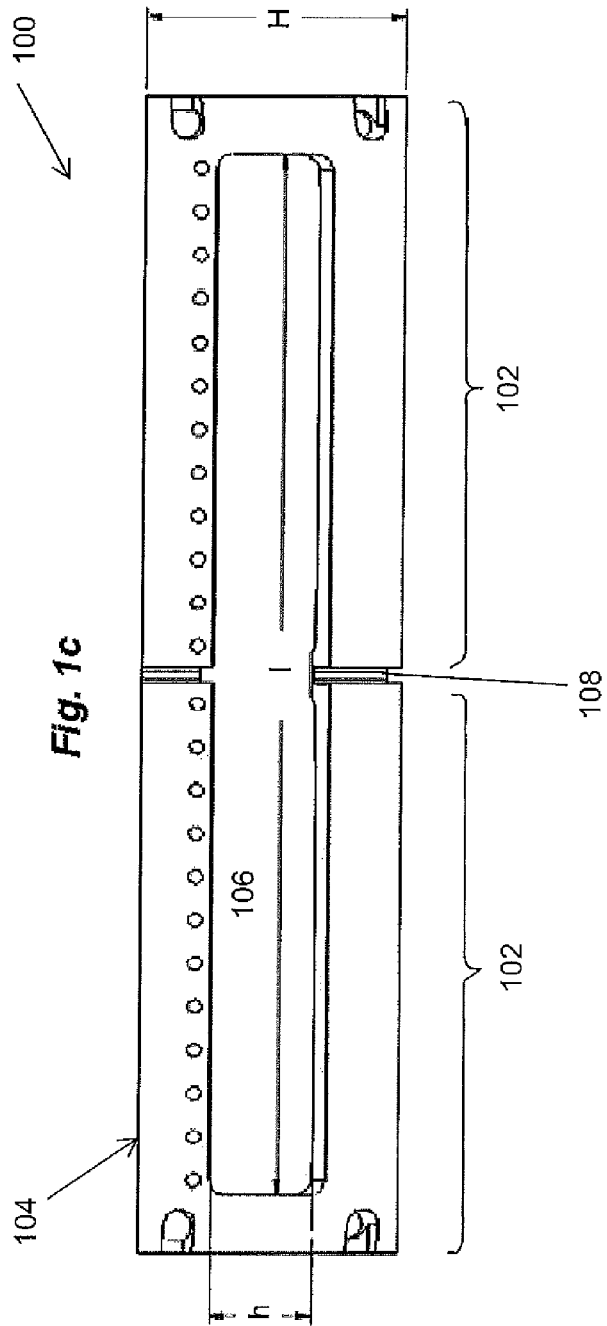

As mentioned, the frame 104 desirably defines a generally rectangular elongated opening 106. As will be seen below, the opening can be defined between two parallel legs of the frame, without the two short sides. According to certain embodiments of skin tensioner and corresponding beneficial method of its use, the length of the opening of the frame 104 is desirably much greater than its height. In the embodiments according to this particular aspect of the present application, as seen in FIG. 1c, the height H of the frame, as well as the length and height h dimensions of the opening 106 are indicated. These dimensions are also shown in several other figures, and the ratio of the length l to the height h in percent is preferably between 10-50%, more preferably between 10-30%. Moreover, the absolute length l of the opening will depend on a particular procedure and the relevant body or skin surface. For example, in hair transplantation application, it may be preferable to have l of at least 40 mm or more so that an adequate length of scalp can be framed for performing a procedure, such as hair follicle harvesting or implantation.

The two segments 102 are configured to be moveable relative to each other, allowing the overall frame 104 to conform to at least a portion of the body surface. In the embodiment illustrated, it can be seen in FIG. 1b that the segments are interconnected in series by a joint, a flexible interconnection 108, in this case formed by creating and using a substantially thinner portion of the frame itself to join the two segments 102. Such a flexible interconnection 108 is commonly known as a "living hinge." Hence, in the illustrated embodiment, the two segments 102 have been created out of the same material, the segments 102 and the flexible interconnection 108 having been formed as an integrated unit, such as by a molding technique, for example.

Figure 1D:
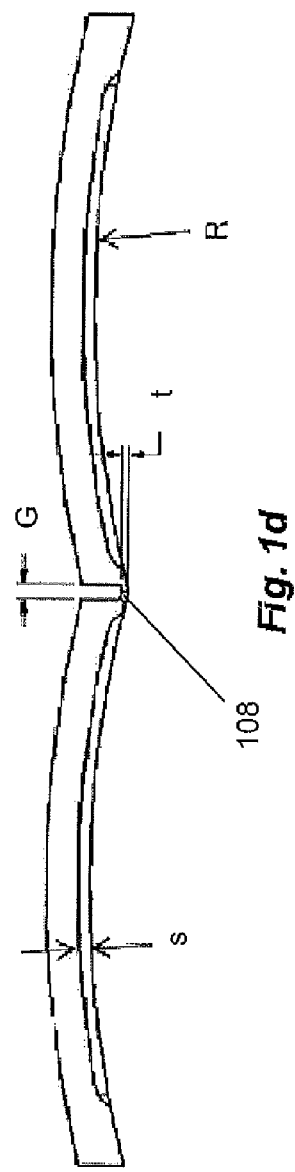

FIG. 1d illustrates an example of interconnection 108, or living hinge, which has a thickness t molded in the homogenous material of the skin tensioner 100. In one embodiment, the thickness is approximately 0.7 mm. To facilitate flexing of the two segments 102, a gap G is provided therebetween above the interconnection 108. For example, the gap may be up to 2 mm, more preferably about 1.6 mm. The gap G facilitates flexing of the two segments 102 about an axis generally parallel to the skin surface, such as to allow bending to conform to the skin surface curvature. Furthermore, the material and thickness of the segments 102 is preferably such that some flexing of each segment is possible. The overall configuration facilitates accommodation of the skin tensioner 100 to various scalp contours.

The disposition of a flexible interconnection 108 between the two segments allows for at least one of the segments to move relative to its adjacent neighboring segment, and allows the combination of two segments to better conform to slight, moderate or more severe variations in the contour of the body surface (for example, around the sides of a patient's head). In some embodiments, the flexibility typically allows for movement in a direction that is substantially orthogonal or at least at an angle to the body surface, but not typically substantially in-plane with the body surface. In this manner movement may be limited to substantially one dimension, thus retaining relative rigidity of the segments in the other two dimensions of a three dimensional environment.

As an alternative the flexible interconnection 108 may be formed from substantially rigid elements that allow for movement of the segments relative to one another. Suitable components, features, and configurations of such a flexible interconnection will be apparent to those of ordinary skill in the art in view of the teachings herein. For example they may take the form of a hinge with a lockable pin or clip. In this manner, once the segments have been moved to conform to the body surface, they can be locked in place. In an alternative example, such a flexible interconnection may include a plurality of pivots or joints. In some embodiments, the flexible interconnection may comprise a spiral-shaped, twisted, bent or other such configuration. In other embodiments, the flexible interconnection can form a lattice or mesh whereby one or more elements can be interconnected (permanently or detachably to allow to extend the overall length of the frame if needed) through linking mechanisms, knots, ties, welds, fusions, or other methods known to those skilled in the art.

In certain embodiments, the underside of the tensioner 100, the surface 110 that faces towards and comes into contact with the body surface, may be contoured, concavely curved as seen in FIGS. 1b and 1d, to better conform to and/or rest closer to the body surface in question when in use. This curvature may ordinarily exist in the tensioner or be apparent when the tensioner is made to conform to the body surface by flexing it at the joint(s). The curvature R (FIG. 1d) may be symmetrical or asymmetrical across the surface, and may be appropriately shaped to fit the body surface in question. In one particular configuration, for example, when used to assist in hair harvesting from a donor area on the scalp or implanting into a recipient area, the combination of undersurfaces from the two segments 102 may comprise a spherical radius to approximate to the shape of the scalp or its desired portion. The upper surface 112 does not have to conform to the body surface, though may follow the shape of the underside for ease of manufacture, cost considerations, and visual appearance.

In use, the frame 104 of the tensioner 100 described herein is configured to conform to a curved body surface by adjusting a relative position and/or curvature of the two segments, such that its underside, or body contact surface 110, can be configured to lie substantially flush against the body surface. The underside or contact surface 110 comprises structures, mechanisms or features for engaging the body surface. One way to engage the body surface is to provide, for example, one or more of body surface grabbers 114 extending from the contact surface 110. In the configuration illustrated, there is only one row of surface grabbers 114, and they are disposed on one elongate leg of the frame 104 only, however, more than one row is contemplated for other embodiments. Tension can be applied to the body surface by adjusting the height h of the opening 106. By applying a force to one or both of the legs away from the other leg, the body surface grabbers 114 transmit the force to the skin surface which results in tension in the region of the scalp within the opening 106. When there is only one row of body surface grabbers 114 on one leg of the frame as shown in FIGS. 1a-1d, the underside 110 of the opposite leg preferably includes a shallow recess, such as shown in FIGS. 1b and 1d. An exemplary spacing s for this recess is between about 1-2 mm. In such an embodiment, securing members or stays (described below) connected along one or both of legs of the frame are attached to surrounding structures such as a headrest or patient chair.

In this particular embodiment, the body surface grabbers 114 take the form of pins that are pushed through the frame 104, from the upper surface 112 such that their heads 116 are visible from the upper surface 112. The heads 116 may optionally serve as fiducials which are described in more detail in reference to FIG. 8. The number of surface grabbers 114 and/or their configuration, and the number of rows and/or their placement is not limited in this regard as will be illustrated later. The surface grabbers 114 may be arranged in multiple rows, or they may be staggered to achieve higher density. Also, some of the surface grabbers 114 may have different depths compared to the other surface grabbers 114, for example, the depth of surface grabbers 114 may range approximately between 1 and 4 mm. For example, one row of surface grabbers 114 may have the same depth of 1 mm while another row of surface grabbers or barbs may have a depth of 2 mm or more. The body surface grabbers 114 may protrude for example from the underside 110 of the body surface tensioning device 100 in the range of 1.5 to 2.5 mm, for example. This length of protrusion is typically sufficient to grab or engage the body surface for tensioning purposes. The body surface grabbers 114 provide an anchor for the frame 104 on the body surface. The disposition of the surface grabbers 114 may be selected by the user, and for example placed where desired, leaving gaps to avoid a location on the patient's scalp that may need to be avoided. However if such user selection is an option, the surface grabbers 114 need to be securely anchored to the frame 104 prior to use of the tensioner 100.

Although body surface grabbers 114 are described herein as a primary example of ensuring good grip to the skin, other solutions that merely increase the coefficient of friction are contemplated as well. For instance, a frame 104 with a contact surface 110 having adhesive may be successfully utilized in conjunction with certain embodiments described herein. Another possibility is mating Velcro patches, with one temporarily adhered to the skin and one to at least a portion of an underside or bottom surface 110 of the frame 104. Alternatively, suction could be utilized in certain embodiments. As such, the term "body surface grabber" as used herein encompasses various structures and ways of engaging the skin or body surface, such as by increasing the lateral resistance to movement of the frame across the skin surface in contrast to a smooth-bottomed surface. That is, "body surface grabber or grabbers" encompass barbs, microbarbs, suction, adhesives, Velcro, ribs, ridges, pins, etc., and even rough surface texture.

Figure 2A:
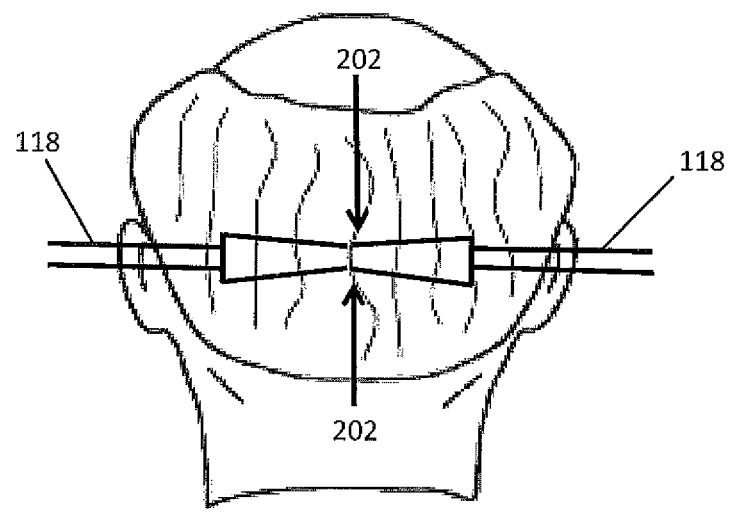
FIG. 2a is a schematic illustration of an example of the compressed tensioning device on the back of a patient's head.

In some embodiments, including those where a skin tensioning device is relatively flexible, may be provided by first compressing the two spaced apart elongated sides of the frame, applying compression forces 202 either manually or using some kind of a tool, to reduce the height of the opening 106, as illustrated schematically in FIG. 2a. Compression may be applied to each or select segments 102 of the frame 104 of FIGS. 1a-b, or along part or substantially the entire length of the frame 104. In the case of the body surface being the scalp of a patient's head as illustrated, once compressed, the body surface grabbers 114 (as seen in FIG. 1b), which for this example will be assumed to be on the upper elongated side of the frame 104, the one furthest from the patient's neck, can be engaged into the patient's scalp. The frame may inherently be compressible due to the selected material of choice, for example, a resilient material, elastic in nature, such as plastic; and/or may be compressible due to shape, structure, gaps, thickness, or other such design choices incorporated into parts of or into the entire frame that render the frame able to compress.

Figure 2B:
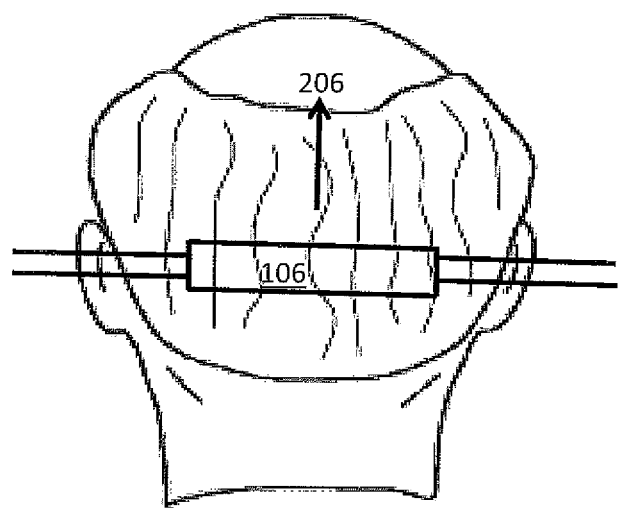
FIG. 2b is a schematic illustration of an example of the decompressed tensioning device on the back of a patient's head.

As illustrated in FIG. 2b, on releasing the compression forces 202, the inherent resilience of the frame 104 causes it to return to its original pre-compressed state, thereby urging the opening 106 to return to its pre-compressed size. Since the body surface grabbers 114 are engaged in the patient's scalp, the scalp moves substantially such that the size of the opening 106 is once again enlarged, causing the patient's scalp to move towards the front of the patient's head, in the direction 206 away from the neck. At least a portion of the slack in the patient's scalp that existed prior to the compression forces being released is taken up, and tension is therefore created in the body surface. Treatment, for example hair harvesting and/or implanting of hair follicles may then be performed.

As seen in FIGS. 1a-b, one or more securing members 118, a first end of which is attached to the shorter side of the frame 104, can be secured via the second ends to a fixed anchoring location such as, for example, the chair on which the patient is placed during treatment. It will be apparent that the securing members 118 may take many and various forms. For example taking the form of a strand, strap, belt, or a band. The shorter ends of the frame 104 may comprise locations in the form of through-bores 120 in the frame 104, which are configured to accommodate and/or anchor the securing member 118. In the embodiment illustrated, these through-bores or internal channels 120 are integrated into the short side of the segment 102, thus utilizing the existing framework, thus not protruding from the upper surface 112 or underside 110 of the frame 104. In some embodiments, instead of through-bores, other forms and structures to aid in temporarily or permanently fastening or anchoring the securing members could be used, for example, notches, ridges, slots or grooves, indents, posts, hooks, or snap-type connections. The securing members 118 are configured to be attached permanently, or temporarily, to the frame 104. The free ends of the securing members 118 are configured to be fixed, or tied, or otherwise connected (including temporarily connected) to a location somewhere other than on the tensioning device 100, for example, a headrest on a chair, or a chair or a couch on which the patient is placed during treatment.

In some embodiment, the securing member 118 primarily holds or secures the skin tensioner 100 against the scalp of the patient. In certain described embodiments where the securing members 118 are attached to the shorter lateral ends of the elongated frame, they may be not primarily used for creating tension in the scalp, but instead provide an anchor of sorts so that the frame does not move. However, as will be explained below in reference to FIGS. 1e and 1f, securing members may also be used primarily to create tension, for example, when connected to the long legs of the frame to apply outward forces such that the body surface grabbers on the legs transmit tension to the underlying scalp. In other words, the securing members may be used primarily to secure the tensioner to the body surface, or primarily to assist in creating or adjusting skin tensioning, or both.

Figure 1E:
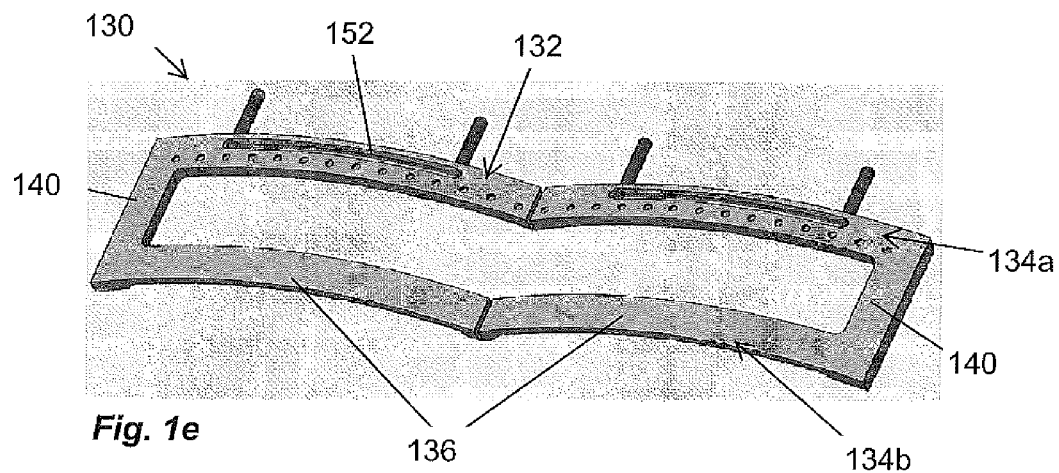
FIGS. 1e and 1f are a schematic perspective views of an example of the upper and lower surfaces of an alternative two-segment elongated skin tensioning device.
Figure 1F:
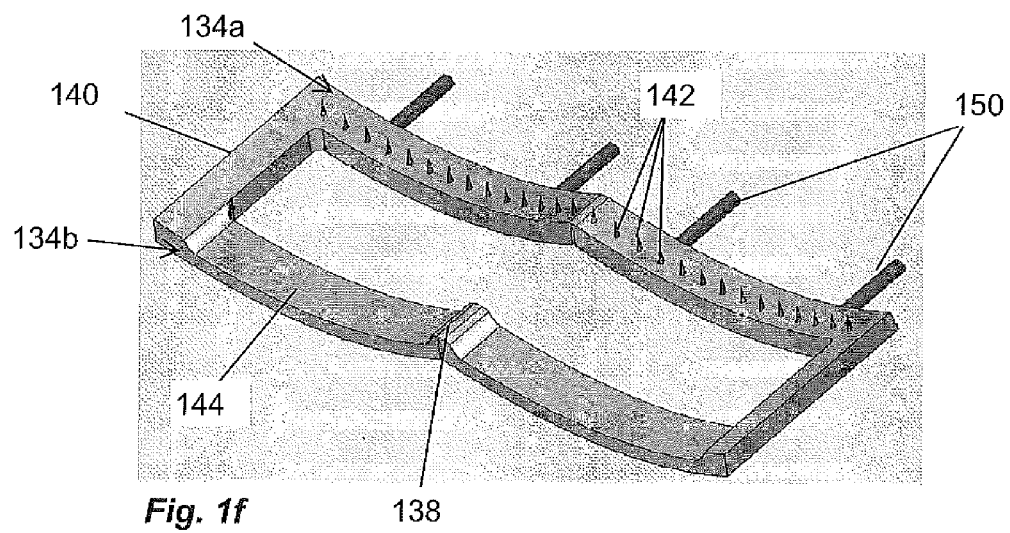

Another example of a skin tensioner 130 of the present application is shown in FIGS. 1e and 1f. As with the first skin tensioner 100 described above, the skin tensioner 130 may comprise a generally rectangular frame 132 defined by a pair of generally C-shaped members connected at living hinges. More particularly, the frame 132 includes a pair of generally parallel elongated legs 134a, 134b each of which is divided into segments 136 in the middle by a living hinge 138. Short sides 140 on the ends of the frame connect the legs 134. As before, an array of body surface grabbers 142 may be disposed along one of the legs 134a, while the other leg 134b includes recesses 144 in each of its segments 136.

In contrast to the earlier embodiment, a plurality of securing members, such as tension bands 150, extends perpendicularly away from each of the segments 136 of the elongated leg 134a having the body surface grabbers 142. In the illustrated embodiment, a tension band 150 may extends through an internal channel 152 formed in each of the segments 136, with its free ends being available to attach to a surrounding structure such as a headrest to apply tension to that segment. There are two tension bands 150 extended away from each segment 136 in the illustrated embodiment, although more than two may be provided.

As indicated earlier, it will be appreciated that the tensioner 100 may comprise any number of segments 102, or combinations thereof. In the alternative embodiment of the invention illustrated in FIGS. 3a-3d, the tensioning device 300 comprises two laterally spaced elongate legs 302, which are coupled to each other at their respective ends 304 thereof, defining a boundary around an opening 306 within which a procedure can be carried out on a tensioned body surface. In the particular arrangement illustrated, each elongate leg 302 comprises three segments 308a, 308b and 308c. Together, the two end segments 308a and 308a are coupled to form a first end section and similarly, the two end segments 308c and 308c are coupled to form a second end section, whereas the middle segments 308b are substantially linear in configuration and generally parallel to each other.

The segments may be of any length, the lengths selected to best suit the body surface and/or patient receiving the treatment. Typically the end segments may be shorter than the linear intermediate segments, and although only three segments are shown, it will be apparent that more and/or longer segments can be utilized for patients with larger relevant body surface area, and fewer and/or shorter segments can be utilized for patients with smaller treatment areas. The segments may be configured to be detachable from one another, and the frame configured to allow adjustment of the number of segments. These various sized and shaped segments may have unique markings or features associated with them, enabling the user to know, for example, that, for example, for a larger head size, they need two blue linear sections, whereas for a smaller head size one purple one would suffice. The unique markings or features may serve to expedite future treatments, for example, allowing the user to identify in the patient's record that a certain configuration of segments was used, so that the same configuration of segments can be used in any subsequent treatment, thus saving preparation time. The two elongate legs 302 are permanently or temporarily coupled together at their respective ends 304, thereby creating a continuous frame circumscribing an opening 306. For example the end 304 of one elongate leg 302 may be temporarily coupled to the end of the other elongate leg by a clip 310, for example.

As in the example described above, there are flexible interconnections 312 between the ends segments 308a/308c and the middle segments 308b of each leg 302. These can form an integrated structure, by forming regions between adjacent segments which are substantially thinner in dimension that the regular segment structure, as described above for the embodiment of FIGS. 1a-1b. Alternatively they may be formed by some type of hinge or other such interconnection which facilitates bending or flexing to better conform to the body surface. In some instances, locking the hinge, clip, or other such interconnection may be desirable.

In this particular configuration, the underside 314 of the frame 300 comprises two rows of body surface grabbers 316, one row on each of the elongate legs 302, the body surface grabbers 316 being substantially evenly distributed along each elongate leg 302, and traversing as far to the ends as possible. However multiple rows may be utilized, depending upon the application and/or patient. If, for example, a patient has a skin type that makes it difficult for the surface grabbers to hold on to, it may be desirable to use segments that have multiple rows of surface grabbers, thereby increasing the chances of the tensioner successfully grabbing onto the skin. In some instance it may be desirable to have only one row of body surface grabbers on the end segments, and multiple rows of body surface grabbers on the middle segments. In other instances it may be beneficial to have multiple rows of body surface grabbers on at least part of the end segments, and only one row of body surface grabbers on the middle row.

Tensioning may be provided by first compressing the two spaced apart elongated legs 302 of the frame toward each other, applying compression forces either manually or using some kind of a tool, to reduce, for example, the height of the opening 306. In the case of the body surface being the scalp of a patient's head, once compressed, the body surface grabbers 316, which in this example are on both the upper and the lower elongated legs 302 of the frame, can be engaged into the patient's scalp. In this particular example, securing members, as described above, can be used to secure the body surface tensioner 300 to the patient's head. In this particular embodiment, the strands are fed through securing member sleeves 318, which may be permanently affixed to the frame, and provide an input and output port for the securing members, a through-bore.

Figure 3A:
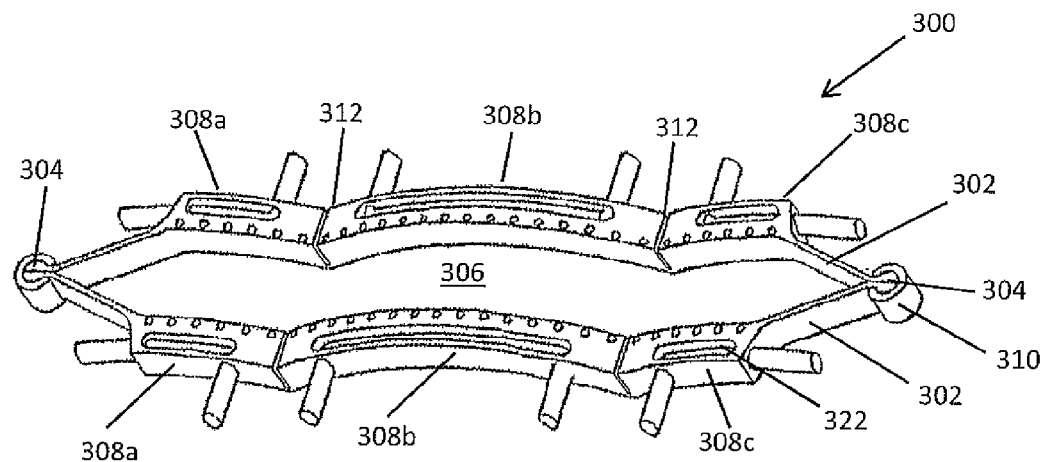
FIG. 3a is a schematic perspective view of the upper surface of another alternative embodiment of a three-segment elongated skin tensioning device.
Figure 3B:
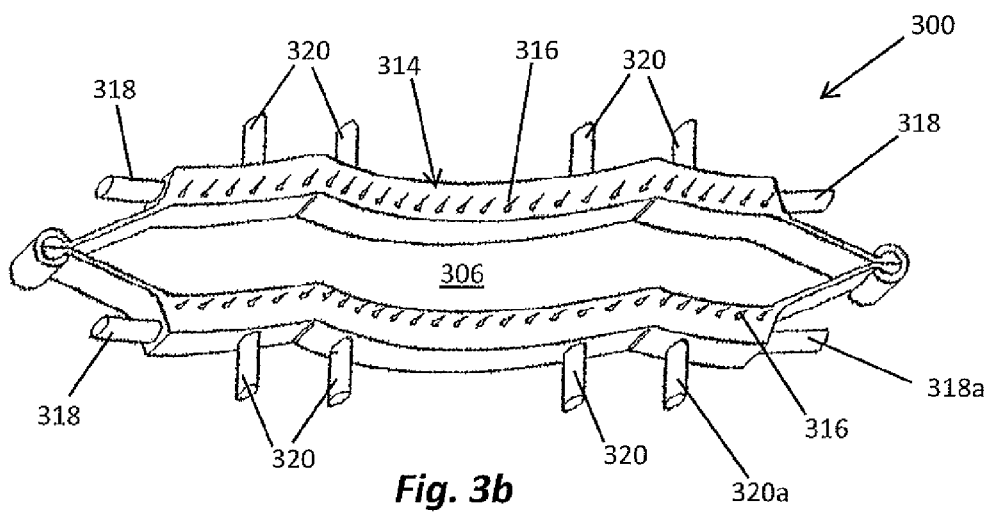
Figure 3C:
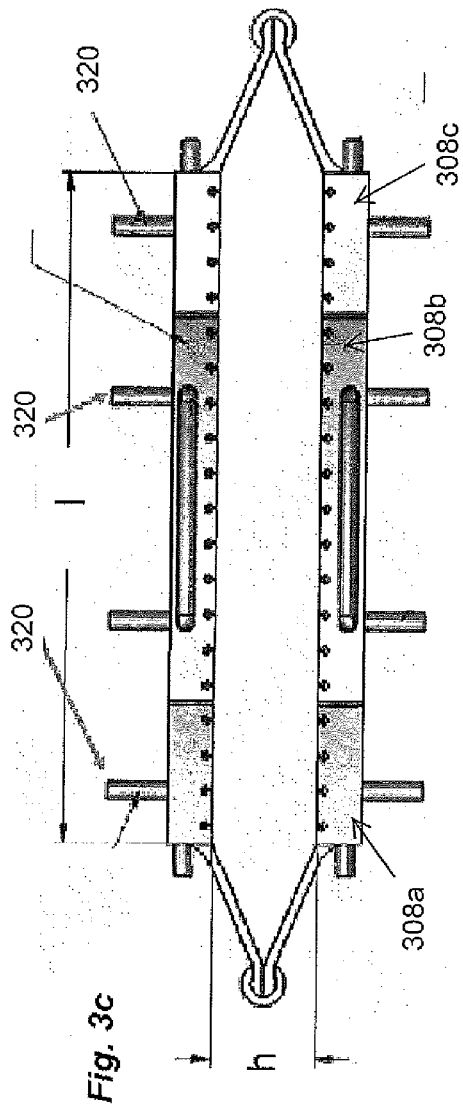
Figure 3D:
Figure 3E:
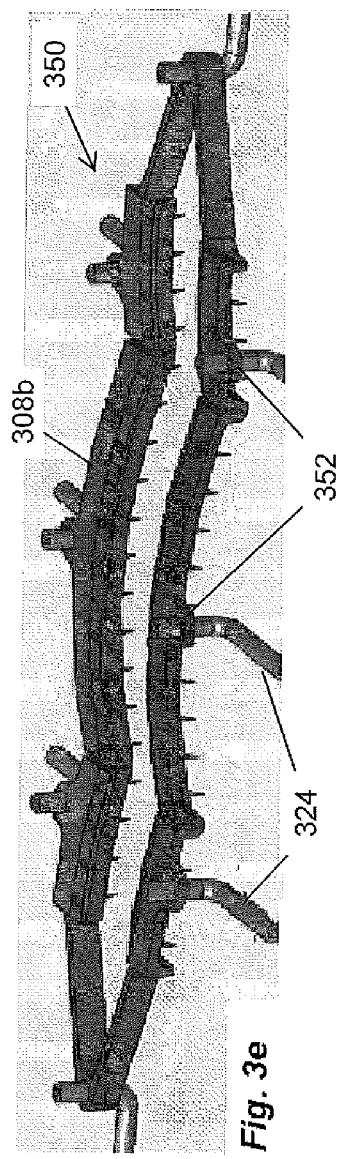
FIG. 3e is a schematic perspective views of the upper surface of yet another example of an alternative three-segment elongated skin tensioning device.
Figure 3F:
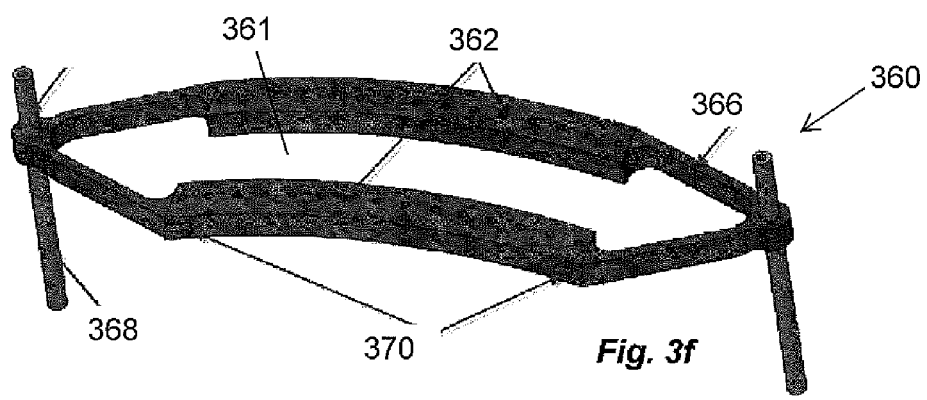
FIGS. 3f and 3g are schematic perspective views of the upper and lower surfaces of another embodiment featuring a one-segment elongated skin tensioning device.
Figure 3G:
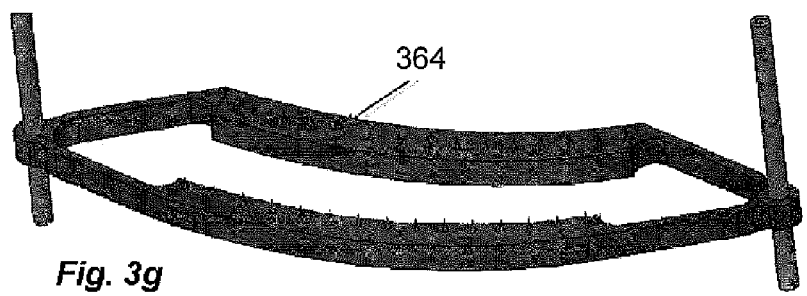
Figure 3H:
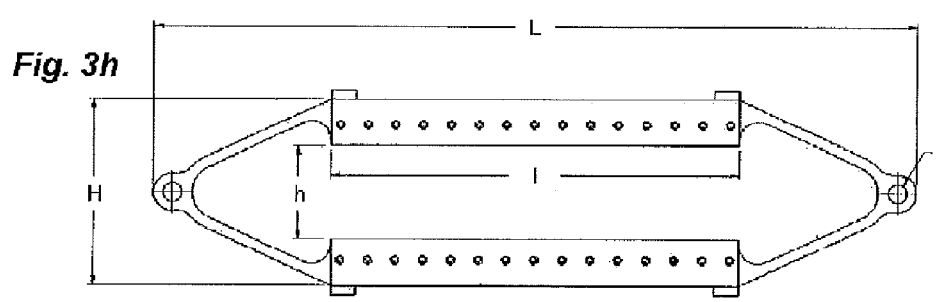
FIGS. 3h and 3i are top plan and side elevational views of the one-segment elongated skin tensioning device of FIG. 3f.
Figure 3I:
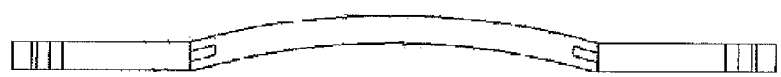

On releasing the frame 300, the inherent resilience of the frame may causes it to return to its original pre-compressed state, thereby urging the opening 306 to substantially return to its pre-compressed size. In this manner, the size of the opening 306 is enlarged from the compressed size, causing tension to be created across the patient's scalp within the opening 306, and within the boundary of the frame. Instead of or in addition to creating tension by the flexibility of the skin tensioning device itself, securing members may alternatively or additionally be used to assist in applying tension to the body surface. In this particular embodiment, the securing members, such as strands, may be fed through sleeves 320 shown in FIG. 3b, which are permanently affixed to the frame, and provide an input and output port for the strands, a through-bore. However, it should be understood that such sleeves 320 are optional and securing members may be attached to the frame by alternative means, for example, threaded through the openings in the frame as described below or as shown in FIG. 3e. Securing member, such as strand or a tension band, can be used to both secure the frame to the body surface and provide tension. In this particular instance, the part of the tension band (not shown) that extends from the sleeve identified as 318a acts primarily as a securing member, whereas the part of the tension band that extends from the sleeve identified as 320a acts primarily as a tensioning mechanism, providing additional tension or at least ensuring that the tension created in the body surface is substantially maintained throughout the procedure. The part of the securing member that extends from the sleeve identified as 318a may also be responsible for allowing additional tension to be provided if necessary to either maintain or alter the tension in the body surface.

According to another aspect of the application, the tensioning device may indicate the amount of tension provided. The tension bands may be disposed within openings which are integrated into the segments 308, thus utilizing the existing real-estate, and not protruding from the upper or lower surfaces of the frame. The securing members (e.g., tension bands) are simply "threaded" in an entry port and out of an exit port, through-bores, holes or openings formed in the respective segments 308. Windows 322 on the upper surface of the frame (as shown in FIG. 3a) allow the user to see the tension band and/or securing member through an open window 322 formed in the segments. Should the tension bands or securing members have markings on them, the user could visually identify the amount of tension provided by the tension band. The movement of the markings along the window 322 may also serve to indicate a change in the tension in the tension band, or perhaps the loosening of the end of a securing member from its anchoring location. FIG. 3e illustrates an alternative three-segment skin tensioning device 350 wherein the tension bands 324 attach to separate eyelets 352 on each of the segments 308a, 308b, 308c. Although only one tension band 324 is shown for each segment, more than one may be provided.

There are numerous ways in which the securing members can be configured. For example, the securing members may be flexible and/or elastic and fixed to the anchoring location on the frame prior to pulling the ends sufficiently to secure them to the desired locations, such as on the patient's chair. Alternatively, the securing member may be flexible and/or elastic and fixed to the desired locations, such as on the patient's chair prior to pulling the free ends sufficiently to secure them to the anchoring locations on the frame. In yet another alternative configuration, the frame may comprise a plurality of through-bore for receiving and anchoring a plurality of strands, which can be also be anchored at locations other than on the tensioning device. In yet another configuration, the securing member may comprise an inelastic strand of fixed length, with tension variation of the strand being provided by a tensioning mechanism such as a knob around which the inelastic strand can be wrapped to provide the tension variation. In a further alternative, the securing member may be inflexible and/or not stretchable. Instead, a selection of multiple alternative anchorage locations may be provided on the chair and/or on the frame of the tensioning device, thus providing an alternative means to achieve the desired tensioning.

In yet a further alternative configuration, the securing member comprises a strand which forms a closed loop configuration (that is, with no free ends). One end of the loop being attached to the anchoring location on the frame, the other end of the loop being attached to the other anchoring location that resides somewhere other than on the frame. This configuration may also further comprise a tension variation device attached to the securing member, providing a means to apply a varied tension to the body tensioning device. The tension variation device may incorporate an inner spool or friction wheel (not shown) for pulling on the associated securing member. For example, the securing member may wrap around a spool rotated by the knob. This provides the user with greater control of the amount of tension in the securing member.

Of course, there are numerous other ways to indicate tension in the securing members, such as more complicated and typically more expensive analog or digital numerical force displays. The present application contemplates any number of indicators from the most simple to the most involved. Tension indicators help the user establish the proper body surface tension. A minimum level of tension is desired, in particular for hair follicle removal to tension the skin surface. Furthermore, a predetermined minimum level of tension helps a removal tool such as a needle pierce the skin without cutting excessive flaps of skin around the follicular unit. However, the tension should be limited to a maximum to avoid excessive trauma to the skin surface. Finally, indicators of tension in each securing member enable the user to balance the amount of tension to avoid applying too much to one location or another.

It will be appreciated that there are other securing member configurations that would adequately serve the purpose which are not limited to having strands or other described structures or elements. It will also be appreciated that the securing member configurations are not limited to structures that require a flexible or elastic member to be stretched, or pulled. Instead, the securing member(s) may be configured, for example, to be non-flexible, and it could be pushed instead of pulled, and still serve the same purpose. The securing member may also comprise, for example, a solid but flexible projection from the tensioning device that can be secured by placing it into a slot with a locking mechanism, such as a thumbscrew, somewhere outside of the tensioning device, for example, on a patient chair. Alternately, the securing member may comprise a slot at a location on the frame, and a solid but flexible projection can be secured to the frame of the device by placing it into the slot. A series of one-way ratchet teeth all inclined in a common direction from one of the ends of the projection may facilitate locking, if the projection is pulled or pushed one way, and enable easy release when encouraged in the opposite direction.

In another example, rather than being in the form of a flexible or elastic member, a configuration that relies upon magnetism, for example, could be utilized. A strip of metal or magnetic material could be disposed on the top surface of the frame, and a magnetic field source could be provided at a location somewhere other than the frame of the tensioning device. The magnet field source could then be activated to provide sufficient magnetic field strength to cause the magnetic material to be attracted in the direction of the magnetic field, and cause the tensioning device to move. The magnetic arrangement may be a semi-permanent one, or permanent. Another example of a securing member is one that utilizes air cylinders or springs. For example, two or more non-flexible strands may be connected by air cylinders or springs. The air cylinders or springs may be configured, when activated, to cause the strands to be either pulled together or pushed apart.

Another feature that may be incorporated into different embodiments of the present application includes fluid flow channels on the skin tensioning device. Saline or other inert fluid may be supplying through a port in the side section and distributed to the treatment area within the frame through the side section, or from around the periphery of the treatment area through all of the side sections. The fluid irrigation will mix with any blood or other fluids in the treatment area, and aspirating ports in the side section provide suction to remove excess fluid. In this regard, a lateral recess in the underside of the side section provides a reservoir which distributes the suction along one side of the treatment area such that a gradient is created to aspirate excess fluid more effectively.

It will be appreciated that in some embodiments and applications the skin tensioning device may be constructed in a manner not conducive to compression. In these instances, without first compressing the tensioning device, the body surface grabbers 316 can be directly engaged into the patient's scalp, and the securing members used to secure the body surface tensioner to the patient's head. Since the body surface grabbers are engaged in the patient's scalp either side of the opening, e securing members can be used to urge the elongated members in a direction away from the opening 306, substantially in the general direction such that the size of the opening is enlarged, causing the patient's scalp to be tensioned. Treatment, for example hair harvesting and/or implanting of hair follicles may then be performed.

One of the advantages of utilizing a segmented body surface tensioning device as described in reference to various figures and embodiments, is that a device can be customized to fit any body shape and size/length. It can also be customized to accommodate any procedure. For example, rather than utilize a scalp tensioner that tensions only a small section of the scalp, the multi-segmented body surface tensioner can be configured to conform to, and tension a strip of the scalp. In this manner, hair can be harvested from, or implanted into, a strip of the scalp, for example from one side of a person's head to the other, in a single procedure without a need to stop.

With reference now to FIGS. 3f-3i, another skin tensioning device 360 is shown that has an overall length L and height H. The frame of the skin tensioning device 360 defines a generally rectangular opening 361 of the frame between a pair of elongated generally parallel legs 362, both of which have body surface grabbers 364 on undersides thereof. In contrast to the earlier embodiments, each of the parallel legs 362 only has one segment. According to this aspect of the disclosure, the material of the legs 362 may be sufficiently flexible alone or together with a slight concave curvature of the underside to conform to most patient's heads. Each of the legs 362 may connect to the other leg via an angled leaf spring 366 that joins with the opposite leaf spring at an eyelet to which a securing member 368 is fastened. The leaf springs 366 provide some inherent resiliency to the frame such that prior to application to the scalp surface the legs of the frame may be compressed together so that they spring apart and apply tension to the scalp therebetween. Alternatively, eyelets or other hooks 370 are provided on the outer wall of each of the legs 362 so that tension bands as described above may be attached for applying an outward force to the legs.

Figure 4:
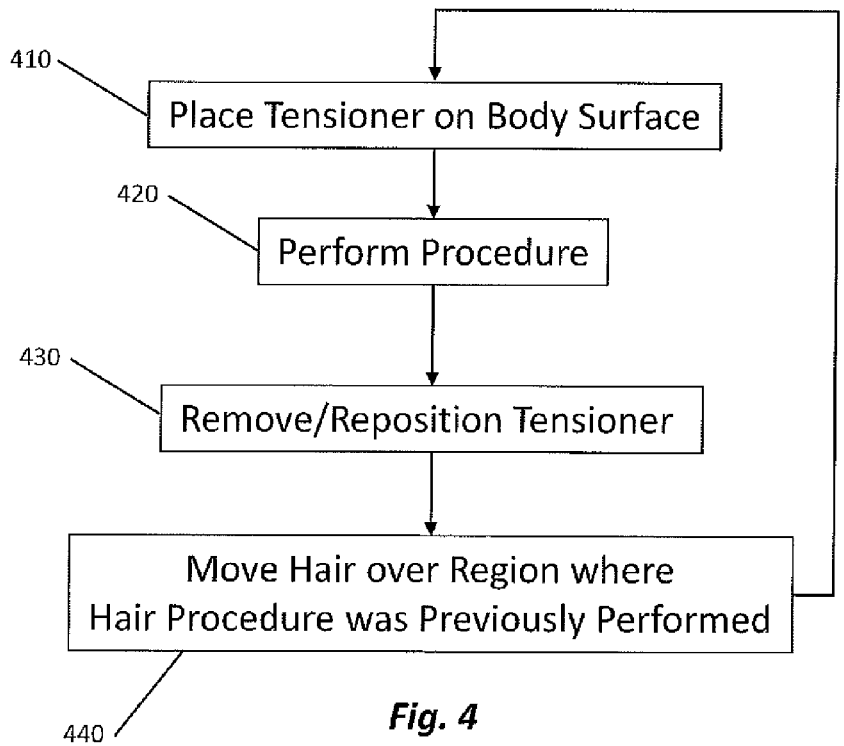
FIG. 4 is a schematic flow diagram illustrating an example of an embodiment representing general methodology of a procedure using skin tensioning devices of the present application.
Figure 5:
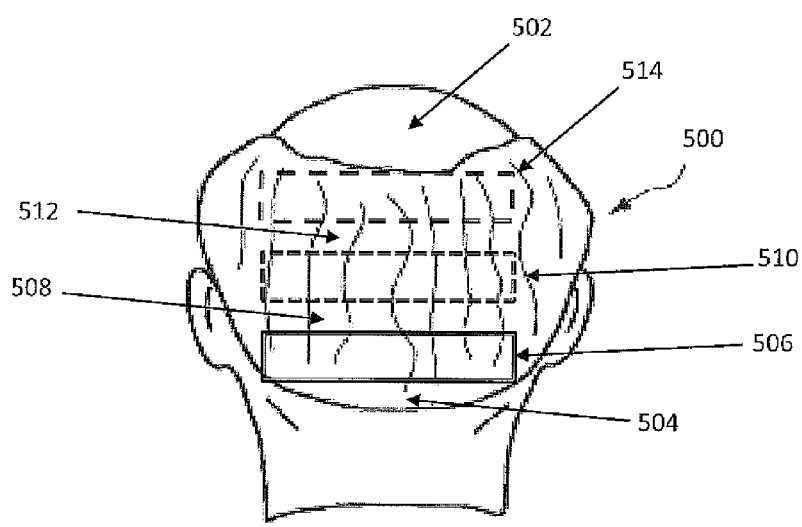
FIG. 5 is a schematic representation of the back of a human head, illustrating treatment planning for a hair transplantation procedure as an example.
Figure 6A:
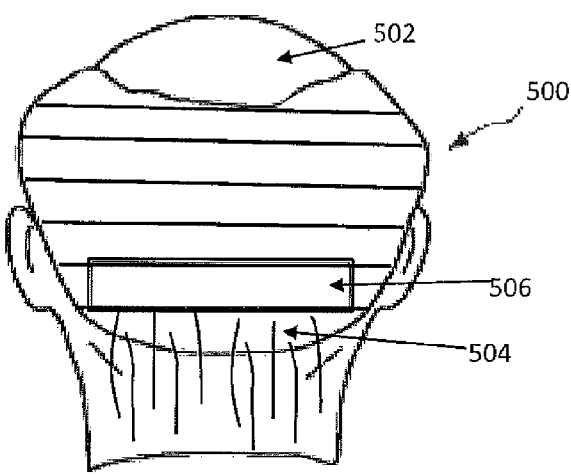
FIGS. 6a-c are schematic representations of the back of a human head, illustrating examples of the placement of a skin tensioning device during a hair transplantation procedure.

According to another aspect of the present application, certain methods for performing a procedure on a body surface utilizing a skin tensioner of the present application are provided. One method of use of the body surface tensioning device according to some embodiments of the present application is illustrated in FIGS. 4 to 6, which are described as an example in reference to hair transplantation procedure. The methodology generally assumes that the user has previously selected an appropriate body surface tensioner to utilize in a patient's hair transplantation procedure, whether that be a pre-formed single or multi-segmented tensioning structure, or selecting the segments and creating a customized body surface tensioner for the patient as described above. The methodology does not describe all details or optional actions that may be performed as appropriate and relevant to a particular procedure. For example, it may be desirable to make sure that a patient is positioned appropriately on a hair transplantation chair and that there are appropriate anchoring structures on the chair, headrest, or other such component of the hair transplantation system. Such steps are not specifically described here. The methodology is described in reference to hair harvesting, but it will be apparent that a similar methodology can be utilized for a patient having hair implanted into his Or her scalp; as well as any other procedures contemplated by the present application.

Generally, when hair harvesting is performed using extraction of individual follicular units, patient may be required to shave large hair donor area, as well as in some instances a recipient implanting area. The same applies to certain hair implantation areas. The method described herein is particularly beneficial to those patients who do not wish to shave or cut very short a large portion of their head prior to having hair harvested therefrom. For those that do not wish to shave a large portion of their head prior to the hair harvesting procedure being performed, use of an elongate or segmented body surface tensioner as described above allows the patient to keep sufficient hair at its original or at least at a longer length than the regions from where hair is to be harvested, such that the regions from where hair is harvested can subsequently be covered or hidden utilizing the original or at least longer length hair. For those that may be embarrassed, self-conscious, or uncomfortable with the idea or having to cut large sections of their hair or in some instances shave at least part of their head to enable a hair transplantation procedure to be performed, this methodology provides a way in which they may still have the procedure performed without undergoing such a drastic change in appearance while enjoying the benefits of the improved tension accomplished with the use of the devices of the present application. In this manner, utilization of the elongated or segmented body surface tensioner potentially caters to a larger audience of prospective hair transplantation clients.

FIGS. 5 and 6 illustrate the head of a patient 500. The upper part 502 of the head 500 is substantially bald, and represents an area for potential implantation. The back portion of the patient's head has an adequate amount of hair for hair transplantation to be considered as an option, the aim being to harvest hair from this back portion to the bald front area. Prior to performing the hair harvesting procedure, the physician or physician's assistant may plan from which regions the hair will be harvested, and which regions the hair will be left, for example, to cover the adjacent region where procedure is performed. FIG. 5 shows the back part of the patient's head, the part with hair divided, as an example, into 6 elongate, generally rectangular regions, each region stretching from one side of the patient's head to the other. The physician or other appropriate user selects which regions hair will be harvested from, and selects which regions hair will be left to provide subsequent coverage for the harvested regions. For the sake of this particular example, it is assumed that first, second, and third regions 506, 510, and 514 are selected as regions from which hair is to be harvested, and that intermediate regions 504, 508, and 512 are selected as regions where hair is to be left to cover and hide the harvested regions. The hair in the selected regions to be harvested, that is regions 506, 510, and 514, is either shaved or cut to a length adequate to allow a hair harvesting procedure to be performed. The hair in the regions selected to be left for coverage purposes, that are regions 504, 508, and 512, is left as its original length or at least at a length longer than the cut or shaved hair.

In some embodiment prior to beginning, at least a portion of hair in the first region 506, or alternatively in all regions selected for harvesting (such as regions 506, 510 and 514), may be shaved to get a relevant area ready for procedure. Step 410 of the procedure begins by placing or positioning the tensioner on the body surface, for example, starting at a lower region of the scalp, closer to the neck, such as first region 506. A lower position is preferable to a higher position as during the hair transplantation process, often fluids, including for example, blood and saline will be present on the body surface, and will typically flow in a direction towards the neck of the patient. However, in certain embodiments the procedure may be performed first at a higher region and then move to the lower regions. In this particular example, illustrated in FIG. 6*a*, it can be seen that hair of original length has been left in region 504, and the harvesting of hairs begins in the first region 506 which has been shaved either before or after placing of the tensioner. While it is easier to shave the relevant area prior to placement of the tensioner, if one wants to limit the shaving only to the portion of an area that corresponds to the opening of the frame of the tensioner or for any other reason, such shaving may be done after the tensioner is placed in the region 506. For simplicity, the hair in the areas above 506 has not been illustrated, and it is assumed that this hair will be directed (e.g., combed) upwards, away from the opening of the body surface tensioning device. Placement of the tensioner may comprise compressing the tensioner prior to engaging the body surface grabbers into the body surface, though as explained earlier, this will depend upon the type of tensioner that is being employed. In certain embodiments using more rigid tensioners, no compression of the tensioner is needed for placement. Placement of the tensioner is such that an elongated opening defined by the frame of the tensioner is over at least a portion of the first region. Having positioned the tensioner at this first region 506, the body surface can be tensioned, for example, as described hereinbefore by utilizing the securing members such as tension bands. When the scalp has been adequately tensioned, the hair harvesting operation can be initiated. The procedure may comprise harvesting all or a subset of the hair accessible via the opening of the body surface tensioner, via manual, semi-automated, or a fully-automated procedure (optionally facilitated by fiducials as described in reference to FIG. 8).

Once the hair from the first region 506 is harvested, the hair that is situated in the intermediate region 508 above the first region 506, but below second region 510, may be directed in the general direction of the patient's neck, that is combed in the downwards direction, such that at least some of the hair in the region 508 covers the sites from where hair has been harvested in the first region 506.

Figure 6B:
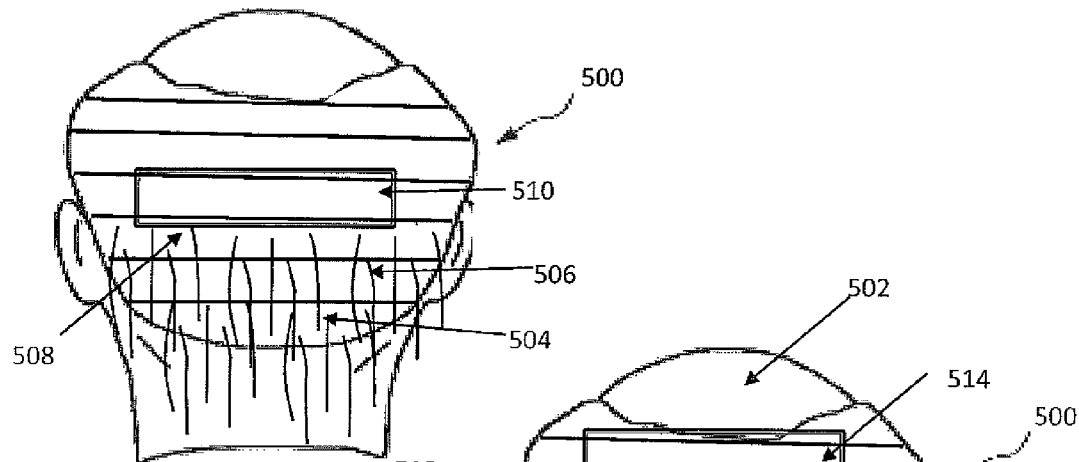

The physician or his assistant may now position the skin tensioner in the next region from where hair is to be harvested, for example, region 510, as illustrated in FIG. 6*b*. If this region 510 has not been already previously shaved ahead of time, then it could be shaved prior to or after placing the skin tensioner. When the scalp has been adequately tensioned, the hair harvesting operation can once again be initiated. As before, the procedure may comprise removing all or a subset of the hair accessible via the opening of the body surface tensioner, and on completion of harvesting within this region, the tensioner can either be removed from the body surface or repositioned to the next region for performing a procedure. On completion, the hair that is situated above region 510, but below region 514, can be directed in the general direction of the patient's neck, that is combed in the downwards direction, such that at least some of the hair in the region 512 covers the sites from where hair has been removed in region 510.

Figure 6C:
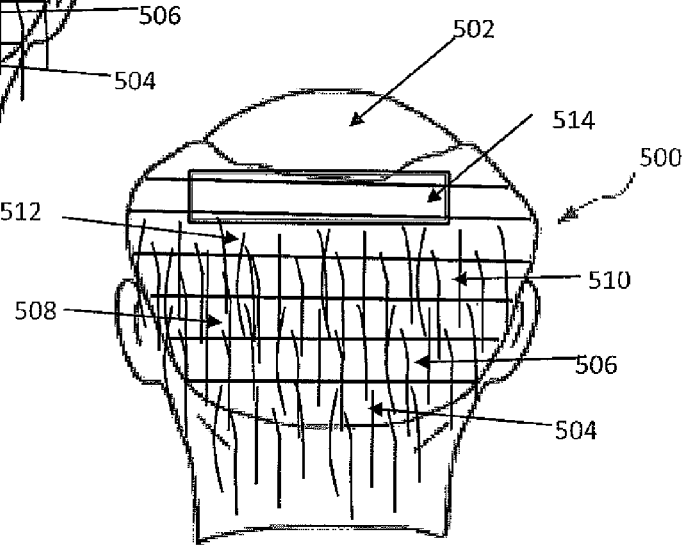

In this manner, hair can be harvested from region 506, 510 and 514, and the sites from where hair has been harvested can be substantially covered by hair disposed in the intermediate regions, that is at least regions 508 and 512. It will be apparent, as indicated in FIG. 6*c*, that the patient is able to have hair harvested from his head, without being embarrassed, self-conscious, and/or uncomfortable as it will not necessarily be apparent that the patient has undergone a hair harvesting procedure. Instead of harvesting, hair can be implanted in a similar fashion, perhaps increasing the density of lesser density hair regions using a similar technique.

According to alternative method, the hair may be shaved or cut as required, after the tensioner is positioned in the region from where hair is to be harvested. In this instance, after the tensioner has been adequately located and secured over a first region of the patient's scalp, the hair within the opening of the frame of the skin tensioner is shaved or cut to length which facilitates the hairs to be more successfully harvested. Typically, this length is in the region of 1 mm. The hair outside the opening may remain at is original length, and need not be cut. The hair harvesting procedure may then be performed at this first region, using a manual, semi-automatic, or automatic hair harvesting procedure. Having harvested the hair desired from within the opening of the skin tensioner in the first region, the tensioner may be moved to the next region and the same sequence may be repeated.

In yet another alternative methodology related to procedures other than hair transplantion, cutting or shaving of the head or other relevant body surface may not necessarily be required, but the general methodology of using intermediate strips of hair between areas where the tensioner is placed and a procedure is performed to cover potentially unsightly regions of the procedure is still beneficial and desirable. According to a general methodology of the present application, a method for performing procedures on a body surface utilizing a skin tensioner is provided. According to certain embodiments, one such method comprises positioning a skin tensioner having a frame over a first region on the body surface where a first procedure is to be performed, the positioning is such that an elongated opening defined by the frame is over at least a portion of the first region; performing the first procedure in the first region and within the elongated opening; positioning the skin tensioner on the body surface over a second region where a second procedure is to be performed such that the elongated opening is over at least a portion of the second region and such that an intermediate region comprising hair follicles is disposed between the first and second regions; directing the hair follicles in the intermediate region in a direction away from the second region; performing a second procedure in the second region and within the elongated opening; and covering at least a portion of one of the first or second regions where the procedure was performed with hair follicles from the intermediate region. The step of performing the procedure of the above method includes, without limitation, not only manual performance of the procedure but also initiating, overseeing or directing any levels of automated performance of the procedure, for example, by directing or overseeing operation of a partially or fully automated device, or computer-assisted device, such as a robotic device, as described in reference to FIG. 9.

It will be apparent that although the methodology described above as discrete steps, one or more steps may be combined or even deleted, without departing from the intended functionality of the embodiments of the invention. It will also be apparent that the methods described above may be performed manually, or they may be partially or substantially automated, including performed using robotic systems. Although described in a manner indicating that hair is harvested from and implanted into the same patient, hair can similarly be harvested from one patient and implanted into another. Alternatively, hair can be received from another source and implanted.

Figure 7:
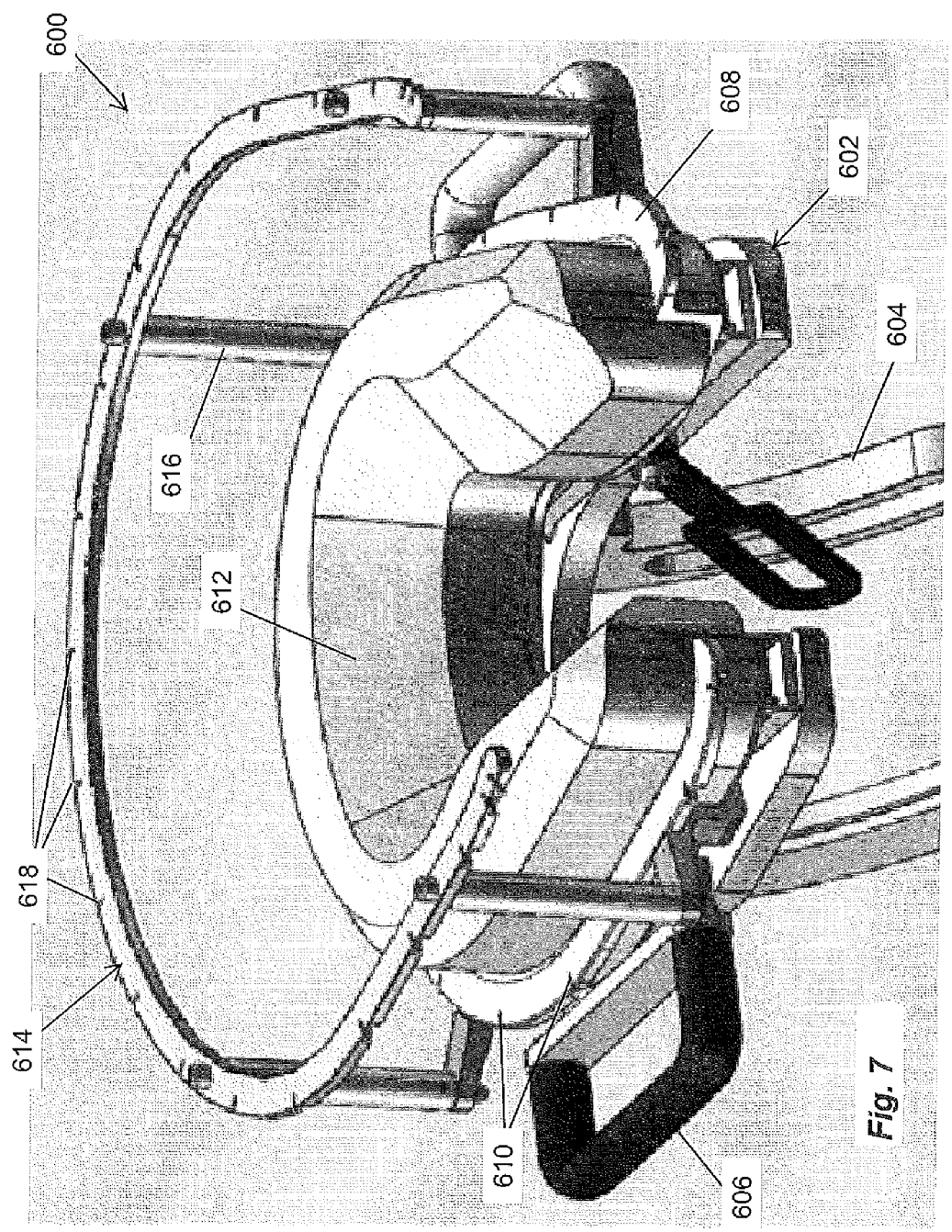
FIG. 7 is a perspective view of an example of a headrest that may be used with the skin tensioning devices of the present application.

FIG. 7 is one example of how any of the skin tensioning device according to the present application may be secured or held stable during the procedure. More specifically, FIG. 7 is a perspective view of an example of a headrest 600 for use with the skin tensioning devices of the present application. The headrest 600 may include a generally C-shaped base 602 that is may be adjustable to various angles, for example, about a pair of curved brackets 604. The headrest may also include a handle 606. In some embodiments, the headrest 600 may be mounted on a patient chair or bed where a particular procedure is performed. The headrest 600 may comprise one or more securing rings. As shown in the example of FIG. 7, a lower securing ring 608 may mount on a linear track mechanism (not numbered) on the base 602. The securing ring 608 includes a plurality of spaced notches or cutouts 610 to which any of the various securing members or tension bands described above can be attached. Thus securing ring 602 may define a cavity within which is positioned a generally C-shaped viscoelastic cushion 612.

An upper securing ring 614 may be permanently or removably mounted above the lower securing ring 608 on a plurality of stanchions 616. The upper securing ring 614 also includes a plurality of spaced notches or cutouts 618 to which the securing members or tension bands can be attached. It is beneficial to make the upper securing ring 614 to be removable to permit greater access to patient's head, if desired.

Figure 8:
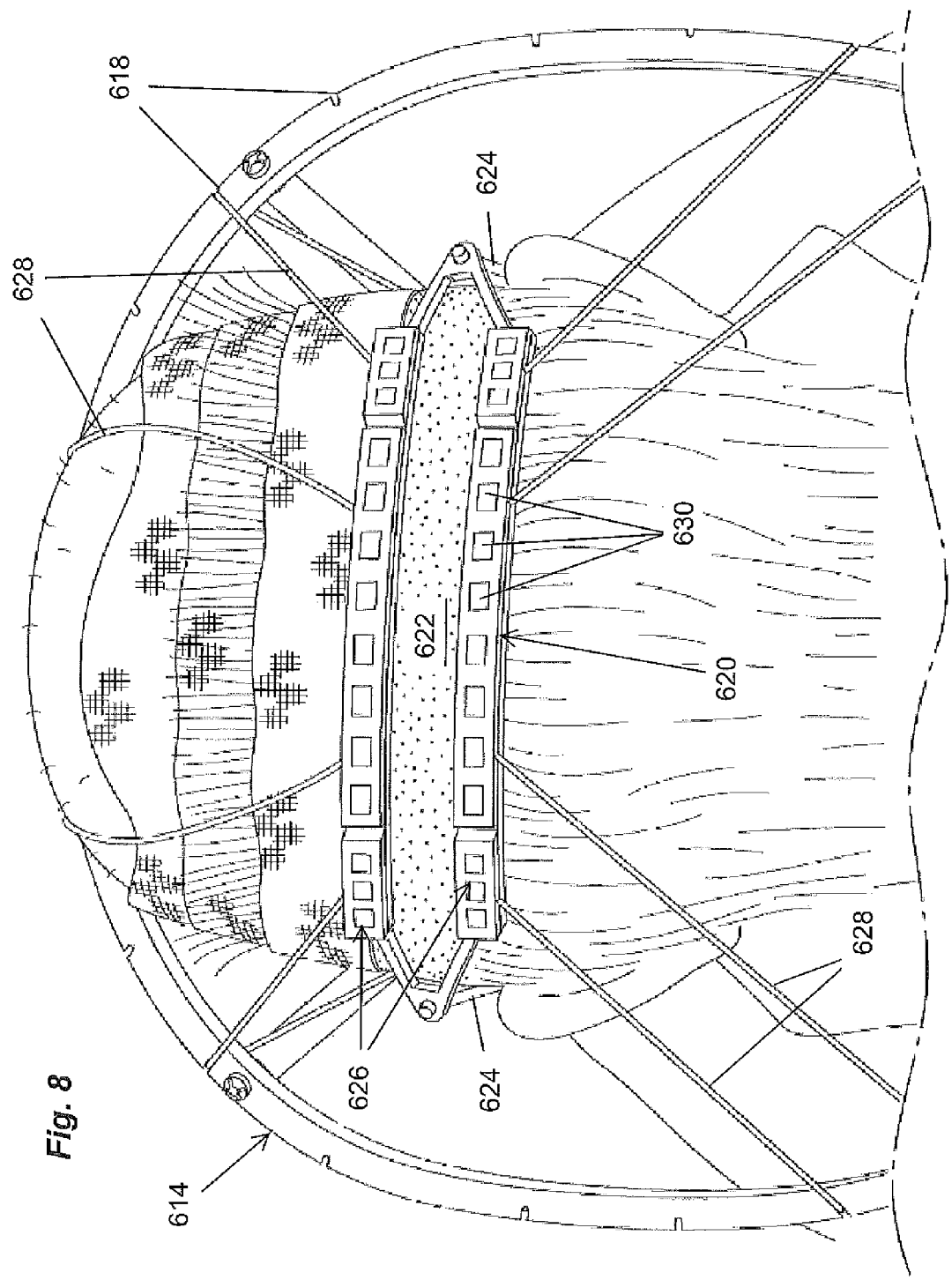
FIG. 8 is a perspective view of a patient positioned in the headrest of FIG. 7 with a three-segment skin tensioning device (shown as an example) positioned over a region of the scalp in which a procedure will be performed.

In use, as seen in the example of FIG. 8, a patient's head is positioned in the headrest 600 of FIG. 7 with his face downward into the opening in the C-shaped cushion 612. By way of example, three-segment skin tensioning device 620, similar to the device 300 shown in FIG. 3a, is positioned with its frame opening over a region or area 622 of the scalp in which a procedure will be performed, such as follicular unit harvesting or implantation. A pair of securing members 624 attach to the lateral ends of the skin tensioning device 620 and are preferably secured to the lower ring 608 of the headrest 600, such as to the notches 610 shown in FIG. 7.

The skin tensioning device 620 includes two parallel legs 626 each having three articulated segments (not numbered). One or more tension bands 628 are secured to each segment of each of the legs 626, and then are attached to or wrapped around the upper securing ring 614, such as to the notches 618. Although not shown, both of the parallel legs 626 of the device 620 desirably have skin grabbing members on their undersides so that tension applied by the bands 628 is transferred to the skin surface. In this manner, the region 622 in which the procedure will be performed is placed under tension.

To facilitate an automated procedure, such as an image-guided or robotic procedure, for example image-guided follicular unit harvesting or implantation, a plurality of Uncials 630 may be provided on the upper surface of the device 620. These unique or distinctive (meaning that they are distinguishable or different from each other) fiducials that are either formed on or affixed to the frame of the skin tensioner 620 and can be visualized by an imaging system. While the fiducials are shown only in reference to present FIG. 8, it should be understood that fiducials may be included in any of the embodiments shown and described in the present application. In other embodiments fiducials could be placed directly on the skin surface, for example, during hair graft implantation. The fiducials may comprise, for example, circular fiducials, each circular fiducial being distinguishable from any other circular fiducial; multiple sets of circular fiducials with each set being distinguishable from any other set; or a set of square fiducials, each square fiducial being distinguishable from any other square fiducial. For example, the fiducials may comprise a single feature, for example a dot, and each fiducial may be distinguishable from the others by the size or color of the feature (e.g., the dot). Alternatively the fiducials may comprise a feature (such as a dot) that may be of the same (or different) size on each fiducial, but the fiducials may be further distinguishable from one another, for example, by the number of the features (such as dots) that each has, or the combination of colors of the dots. In further alternative embodiments, each fiducial may comprise a different feature or features. The fiducials can be of any shape or configuration, provided the imaging system is capable of distinguishing one fiducial from another. The fiducials may be placed at a known distance away from the inner edges that form the central opening of the frame of the skin tensioner, and may be placed symmetrically or asymmetrically. Alternatively, a distance may be measured from the inner edge of the skin tensioner to a center of the relevant fiducial. For example, in some embodiments the row of fiducials is placed such that the distance may range between 1 mm and 10 mm (and in some embodiments may further range between 2 mm and 4 mm) from the inner edges of the frame. In other embodiments, depending on the application, this distance may have widely different ranges. Fiducials may be used to bound an area, for example, for harvesting or implanting, and are especially useful when the tensioner is used in robotic or other image-guided procedures. Such fiducials may provide reference points to guide a robotic system, such as one described by example in reference to FIG. 9 below.

FIG. 8 also illustrates an example of a method of directing hair adjacent to each of the legs 626 out of the way so that the region 622 is clear. Namely, the hair that is below the region 622 is combed downward, while the hair above is combed up and may be covered by a band to keep it up temporarily, as shown in FIG. 8. After performing the follicular unit harvesting or implantation, the device 620 is removed and the hair above the region 622 is combed downward to cover it. In this manner, thin elongated strips of scalp corresponding to the opening of the frame of the skin tensioner can be treated, with regions of hair in between that can subsequently cover up any bare patches.

Figure 9:
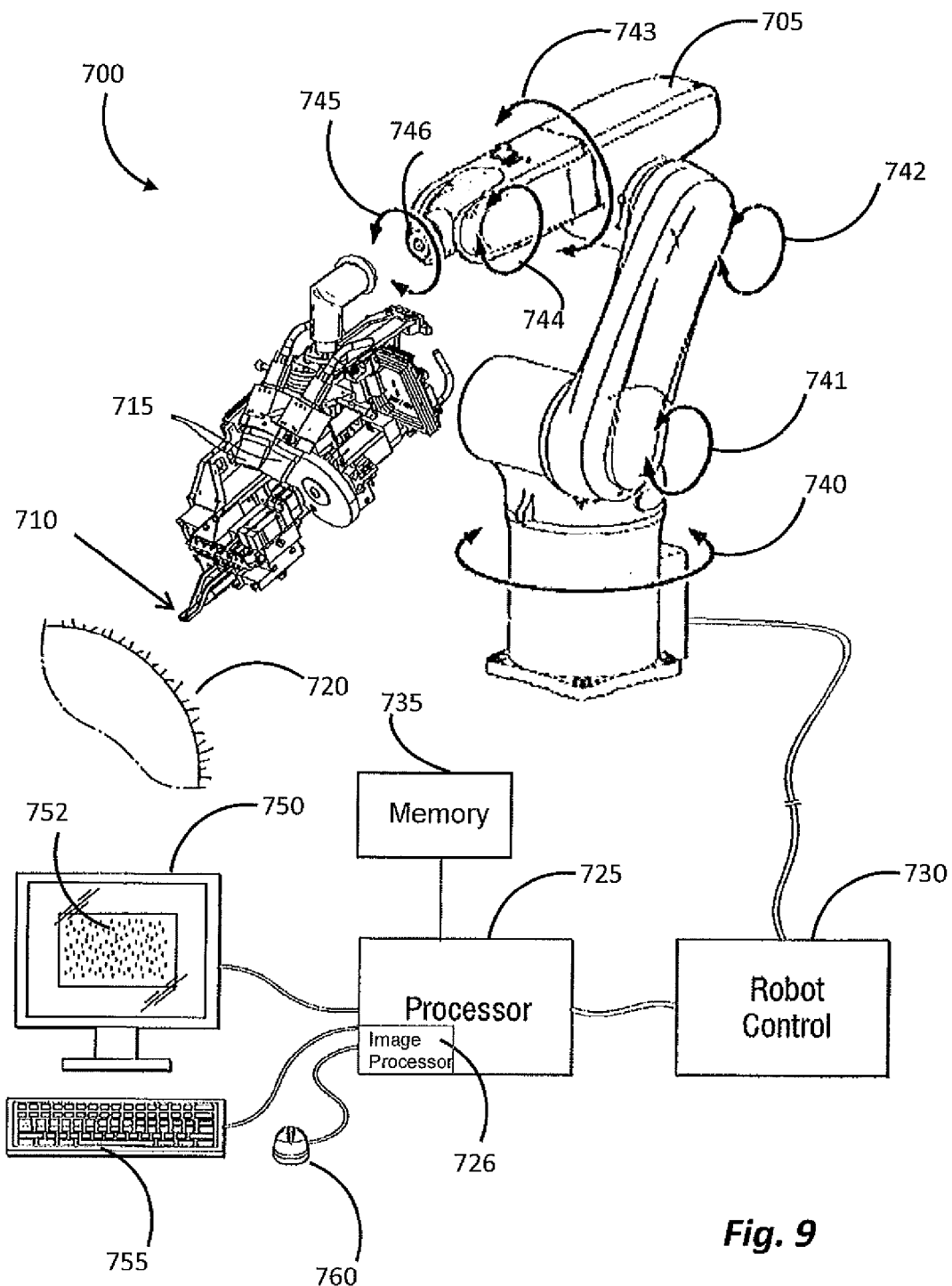
FIG. 9 is a schematic view of an example of a robotic system for performing a procedure with the assistance of any of the various skin tensioning device disclosed herein.

FIG. 9 illustrates an example of a robotic system that could be used with the skin tensioning devices and methods of the present application. The example of FIG. 9 is s schematic representation of a robotic system 700 for harvesting and/or implanting follicular units into a body surface. The system 700 includes a movable arm 705 to which is coupled a harvesting or implanting tool 710. The tool 710 is preferably mounted to a distal end plate or flange 746 of the movable arm 705, but is illustrated detached from the movable arm 705 in FIG. 9. Various motors and other movement devices may be incorporated to enable fine movements of an operating tip of the tool 710 in multiple directions. The robotic system 700 further includes a camera system or image acquisition device 715, which may be mounted in a fixed position, or coupled (directly or indirectly) to the movable arm 705 or other controllable motion device. The operating tip of the tool 710 is shown positioned over a body surface 720, in this case a part of a patient's scalp having hair follicles thereon.

The robotic system 700 includes a processor 725 that is configured to be operatively coupled to the imaging system 715, a robot controller 730, and a memory 735. The processor 725 may comprise an image processor 726 for processing images obtained from the imaging system 715. The image processor 726 may be a separate device or it may be incorporated as a part of the processor 725. Image data acquired by the imaging system 715 is processed via the image processor 726, the processor 725, or both, and the processor 725 provides control signals to the robot controller 730 for directing movement of the arm 705. In particular, images are acquired from the imaging system 715. The acquired images are digitized using image segmentation techniques implemented in software stored in the memory 735 in order to identify the position(s) and orientation(s) of objects of interest.

The processor 725 instructs the various movement devices of the robotic system, including the movable arm 705 and the tool 710, acting, for example, through the controller 730. The controller 730 may be operatively coupled to the movable aim 705 and configured to control the motion of the arm 705, including the motion based on the images or data acquired by the camera system 715. Alternatively, the controller 730 may be incorporated as a part of the processor 725, so that all processing and controls of all movements of all the various tools, the movable arm 705 and any other moveable parts of the assembly, including those based on the images or data acquired by the camera system 715, are concentrated in one place.

The movable arm 705 may includes six rotational axes having associated therewith one or more motors (e.g., one motor may cause rotation about one axis or multiple axes or multiple motors may work together to cause rotation about a single axis) and encoders. The movable arm 705 may include fewer or more than six rotational axes. In response to instructions received from the processor 725, the controller 730 generates one or more control signals that cause one or more motors to cooperatively move the tool 710 to a desired position and orientation.

The robotic system 700 may further include any number of input or output devices, such as a monitor 750, keyboard 755, and mouse 760. A magnified image 752 of the body surface 720 is illustrated on the imaging display or monitor 750. In addition, the system 700 may comprise other tools, devices, and components useful in harvesting and/or implantation of the hair follicles, or in hair treatment planning. Various parts of the system allow an operator to monitor conditions and provide instructions, as needed. For example, the system 700 may further comprise an interface (not shown) adapted to receive image data. The processor 725 may interact with the imaging system 715 via the interface. The interface may include hardware ports, cables, leads, and other data transmission means, or it may comprise a computer program.

Some non-limiting examples of the imaging system 715 illustrated in FIG. 9 include one or more cameras, such as any commercially available cameras. An example image acquisition or imaging device may be held, for example, by the movable arm 705, or by any other mechanism or means. Of course, various image acquisition devices or a combination of several devices could be used with any of the examples described herein. For example, 3D vision can be achieved in multiple ways, including without limitation using multiple cameras, or using a single camera paired with an external sensor, such as a laser range finder. The cameras used may be of various combinations of different sizes, color/grayscale, visible light/IR or UV, etc. While the camera system 715 preferably comprises a device that takes still images, the camera system 715 may also comprise a device capable of real time imaging (e.g., a webcam capable of continuously streaming real time or video information), and/or the camera system 715 may also have a video recording capability (e.g., a camcorder). The imaging system 715 may be digital or analog and it may be coupled to the processor 725 to control the imaging operation and to process image data.

The processor 725 preferably operates as a data processing device, which, for example, may be incorporated into a computer. The processor 725 may include a central processing unit or parallel processor, an input/output interface, a memory with a program, wherein all the components may be connected by a bus. Further, the computer may include an input device, a display, and may also include one or more secondary storage devices. The bus may be internal to the computer and may include an adapter for receiving a keyboard or input device or may include external connections.

The processor 725 may execute a program that may be configured to include predetermined operations and methods. The processor 725 may access the memory 735 in which may be stored at least one sequence of code instructions comprising the program for performing predetermined operations. The memory 735 and the program may be located within the computer or may be located external thereto. By way of example, and not limitation, a suitable image processor 726 may be a digital processing system that includes one or more processors or other type of device. For example, a processor and/or an image processor may be a controller or any type of personal computer (PC). Alternatively, the processor may comprise an Application Specific Integrated Circuit (ASIC) or Field Programmable Gate Array (FPGA). It will be understood by skilled persons that the processor and/or the image processor for use with the present disclosure is programmed and configured to perform various image processing techniques, for example, segmentation, edge detection, object recognition, and selection. These techniques are generally known and therefore are not separately described here.

The imaging display device 750 may comprise a high resolution computer monitor which may optionally be a touch screen. The imaging display may allow images, such as video or still images, to be readable and for follicular units, and parts thereof, to be visualized. Alternatively, the imaging display device 750 can be other touch sensitive devices, including tablet, pocket PC, and other plasma screens. The touch screen may be used to modify the parameters of the hair transplantation procedure, directly through the image display device.

Use of such a robotic system with a skin tensioning device of the present application may enable one to plan and perform partially or fully automated hair harvesting or hair implantation procedures. For example, an imaging system may capture an image of a fiducial located on a skin tensioner device that is placed on a patient's head and may capture an image of a hair follicle itself. From this information, it is possible to determine a position of the hair follicle relative to the fiducial (e.g., to help plan a path across a patients scalp).

Figure 10:
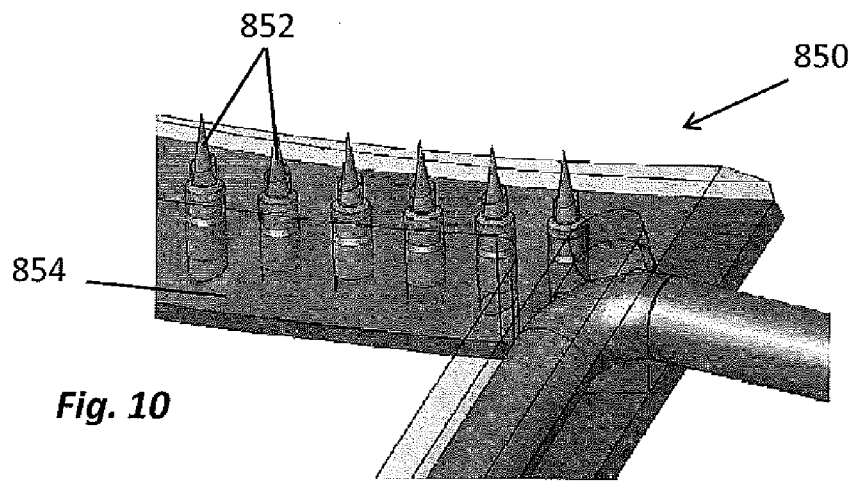
FIG. 10 is a perspective view of a portion of the underside of a skin tensioning device disclosed herein showing as an example an array of sharp pins that may be used to apply a grabbing force to a body surface.

Turning now to FIG. 10, as mentioned above, the body surface grabbers used with the various skin tensioning devices disclosed herein can take a number of forms, including pins that are pushed through the device frame from the upper surface. FIG. 10 is a perspective view of a portion of the underside of a skin tensioning device 850 showing an array of sharp pins 852 used to apply a grabbing force to a body surface. The pins 852 are installed through holes from an upper surface of at least one of the legs 854 of the device 850 such that their pointed ends 856 project below the lower surface. The holes in the device 850 may be oriented perpendicular to the legs 854 such that the pointed ends 856 extend directly downward, or the holes may be angled such that their pointed ends projects slightly outward toward the direction of tension applied by the tension bands. The latter configuration helps improve anchoring on the skin surface and reduces the chance of tearing of the skin.

Figure 11A:
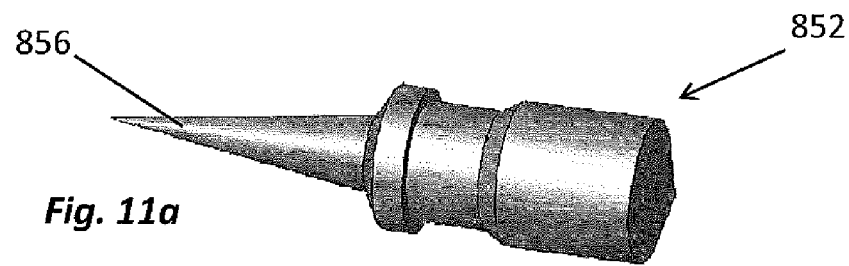
FIG. 11a is a perspective view of one of the pins from FIG. 10.
Figure 11B:
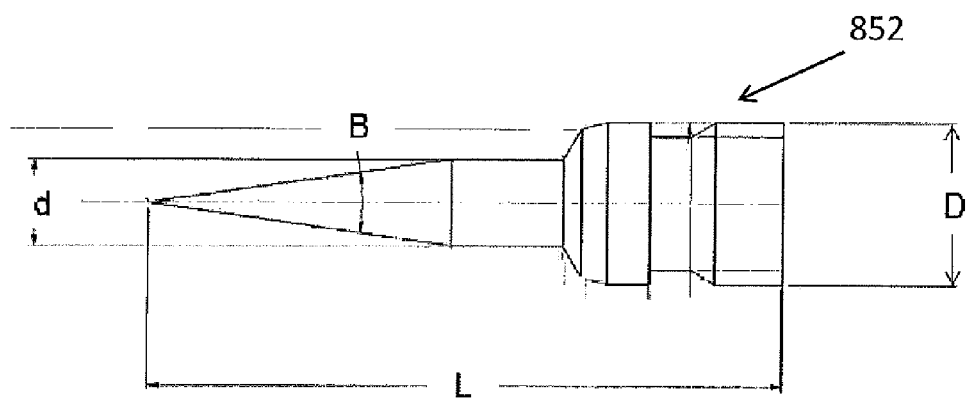
FIG. 11b is a side elevational view of an example of the pin of FIG. 10.

FIG. 11*a* is a perspective view of one of the pins 852, while FIG. 11*b* is a side elevational view showing several significant dimensions. In a representative embodiment, the overall length L of the pins 852 is between 5-6 mm, while the diameter D of a base portion is about 1.5 mm. A diameter d of a shaft portion leading to the pointed end 856 is about 0.8 mm, while the angle B of the pointed end is desirably between 15-20°. Of course, these dimensions may be adjusted depending on various factors, such as the thickness of the frame, etc. Various polymer or metallic materials can be used for the pins 852, though stainless steel is preferred for its corrosion resistance and ability to be sterilized and reused without dulling.

The foregoing illustrated and described embodiments of the present application are susceptible to various modifications and alternative forms, and it should be understood that the inventions as generally disclosed herein, as well as the specific embodiments described herein, are not limited to the particular forms or methods disclosed, and that many other embodiments are possible within the spirit and the scope of the present inventions. Moreover, although individual features of one embodiment may be discussed herein or shown in the drawings of the one embodiment and not in other embodiments, it should be apparent that individual features of one embodiment may be combined with one or more features of another embodiment or features from a plurality of embodiments. By way of non-limiting example, it will be appreciated by those skilled in the art that particular features or characteristics described in reference to one figure or embodiment may be combined as suitable with features or characteristics described in another figure or embodiment. Furthermore, the methodologies described can be applied to any treatment, and is not limited to hair transplantation.

It will be further appreciated by those skilled in the art that the invention is not limited to the use of a particular system, and that automated (including robotic), semi-automated, and manual systems and apparatus may be used for positioning and actuating the respective removal tools and other devices and components disclosed herein. While the invention has been described in its preferred embodiments, it is to be understood that the words which have been used are words of description and not of limitation. Therefore, changes may be made within the appended claims without departing from the true scope of the invention.

What is claimed is:

1. A method for performing a procedure on a body surface utilizing a skin tensioner, comprising:
    positioning a skin tensioner having a frame over a first region on the body surface where a first procedure is to be performed, the positioning is such that an elongated opening defined by the frame is over at least a portion of the first region;
    performing the first procedure in the first region and within the elongated opening;
    skipping a first intermediate region, wherein the first intermediate region comprises a region where hair follicles are not harvested, and positioning the skin tensioner on the body surface over a second region where a second procedure is to be performed such that the elongated opening is over at least a portion of the second region and such that the first intermediate region is disposed between the first and second regions;
    directing the hair follicles in the first intermediate region and/or a second intermediate region which is adjacent the second region in a direction away from the second region, wherein the second intermediate region comprises a region where hair follicles are not harvested;
    performing a second procedure in the second region and within the elongated opening; and
    directing hair follicles from the first or the second intermediate region to cover at least a portion of one of the first or second regions where the procedure was performed.

2. The method of claim 1, wherein prior to performing the first procedure in the first region, hair follicles positioned adjacent the first region are directed away from the first region without being removed from the body surface.

3. The method of claim 1, wherein a body surface is a scalp and the second region is located below the first region, and wherein the directing to cover step comprises combing the hair follicles from the first intermediate region to cover at least the portion of the second region.

4. The method of claim 1, further comprising shaving or cutting hair follicles in the first and/or second regions prior to positioning the skin tensioner over the respective first and/or second region.

5. The method of claim 4, wherein the covering step comprises covering with the hair follicles from the first and/or the second intermediate region the shaved portion of the first and/or second region.

6. The method of claim 1, wherein the first and the second procedure comprises a hair transplantation procedure.

7. The method of claim 1, wherein performing the first procedure comprises directing operation of a robotic system.

8. The method of claim 1, further comprising conforming the skin tensioner to the curvature of the first and/or the second region.

9. The method of claim 1, further comprising using one or more securing members to adjust tension applied by the frame of the skin tensioner to the body surface.

10. The method of claim 9, the method comprising attaching a first end of the one or more securing members to the frame of the skin tensioner and a second end of the one or more securing members to a location other than the skin tensioner.

11. A method for performing a procedure on a body surface utilizing a skin tensioner, comprising:
    selecting a first region where a first procedure is to be performed;
    positioning on the body surface a skin tensioner having a frame such that an elongated opening defined by the frame is over at least a portion of the first region;
    operating or directing operation of a tool to perform the first procedure in the first region and within the elongated opening;
    skipping an intermediate region, wherein the intermediate region comprises a region where hair follicles are not harvested, and selecting a second region where a second procedure is to be performed such that the intermediate region is disposed between the first and second regions;
    directing the hair follicles in the intermediate region in a direction away from the second region;
    positioning the skin tensioner on the body surface such that the elongated opening is over at least a portion of the second region;

operating or directing operation of the same or a different tool to perform a second procedure in the second region and within the elongated opening; and redirecting hair follicles from the intermediate region to cover at least a portion of one of the first or second regions where the procedure was performed with the hair follicles from the intermediate region.

12. The method of claim 11, wherein the frame comprises a plurality of segments that are dettachable from each other, the method comprising adjusting a number of the segments to be coupled such that the frame spans a desired body surface.

13. The method of claim 12, wherein the plurality of segments comprise flexible interconnections therebetween, and the method comprises bending or flexing the frame to conform to the body surface.

14. The method of claim 11, wherein the frame comprises at least two laterally spaced elongate legs, and the method comprises permanently or temporarily coupling the elongate legs at their respective ends.

15. The method of claim 11, wherein the method comprises customizing configuration of one or more segments of the frame and recording configuration of segments for use in a subsequent procedures.

16. The method of claim 11, wherein the first and the second procedure comprises a hair transplantation procedure, and the method further comprises positioning a patient's head in a headrest with the patient's face directed downward into an opening of a cushion.

17. The method of claim 16, further comprising using one or more securing members to adjust tension applied by the frame of the skin tensioner to the body surface, the one or more securing members attached at one end to the frame and another end to the headrest.

18. The method of claim 6, wherein the hair transplantation procedure comprises a hair implantation procedure.

19. The method of claim 6, wherein positioning the skin tensioner over the first region comprises positioning the skin tensioner over a lower region of the scalp, closer to the neck, and positioning the skin tensioner over the second region comprises positioning the skin tensioner over a higher region of the scalp, further from the neck.

20. The method of claim 1, further comprising applying compression forces to the frame either manually or using a tool.

21. The method of claim 1, further comprising supplying saline or other inert fluid for distribution over an area where the first or second procedure is performed.

22. The method of claim 21, further comprising using suction to remove excess fluid.

23. The method of claim 20, comprising using inherent resilience of the frame to cause the frame returning to its pre-compressed state.

24. The method of claim 1, further comprising using one or more rows of body surface grabbers located on the frame to increase the chances of the tensioner successfully grabbing onto the skin.

25. The method of claim 7, wherein the frame comprises fiducials, the robotic system comprises a robotic arm and an image acquisition device, and the method comprises guiding movement of the robotic arm based on the fiducials.

26. The method of claim 11, wherein the frame comprises a tension variation device, the method comprising applying a varied tension to the frame.

27. The method of claim 1, wherein the frame comprises one or more tensioner indicators, and the method comprises using the one or more tensioner indicators to ensure a minimum level of tension is established over the body surface and to ensure that a maximum level of tension is avoided.

28. A method for performing a procedure on a body surface utilizing a frame, comprising:

identifying one or more regions where a procedure is to be performed;

identifying one or more intermediate regions adjacent the one or more regions, wherein in one or more intermediate regions hair follicles are not removed and kept at either their original length or cut to a length sufficient to cover procedure sites of at least one of the adjacent one or more regions;

positioning on the body surface a frame such that an elongated opening defined by the frame is over at least a portion of a first of the one or more regions;

directing the hair follicles in one or more of the one or more intermediate regions adjacent the first region in a direction away from the first region;

operating or directing operation of a tool to perform the first procedure in the first region and within the elongated opening;

skipping an intermediate region disposed between the first and a second region of one or more regions to position the frame on the body surface such that the elongated opening is over at least a portion of the second region where a second procedure is to be performed;

directing the hair follicles in one or more of the one or more intermediate regions adjacent the second region in a direction away from the second region;

operating or directing operation of the same or a different tool to perform the second procedure in the second region and within the elongated opening; and redirecting the hair follicles from the one or more intermediate regions to cover at least a portion of one of the first and/or second regions where the procedure was performed.

29. The method of claim 28, the method comprising customizing the size, shape and/or length of the frame by selecting the size and/or number of segments to be coupled to form a frame.

30. The method of claim 28, wherein the procedure comprises a hair harvesting procedure, a hair implantation procedure, a hair transplantation procedure, biopsy procedure, or a dermatological procedure.

31. The method of claim 28, wherein the frame comprises a plurality of segments with flexible interconnections therebetween, the method comprising adjusting the flexible interconnections such that the frame conforms to the body surface.

32. The method of claim 31, wherein adjusting the flexible interconnections allows movement in a direction that is substantially orthogonal or at an angle which is not substantially parallel to the body surface.

33. The method of claim 28, wherein the steps of directing the hair follicles away from the first or the second regions comprises directing the hair follicles in an upward direction if the intermediate region is disposed above the first or the second region and directing the hair follicles in a downward direction if the intermediate region is disposed below the first or the second region.

34. The method of claim 33, further comprising covering the hair follicles directed in the upward direction with a band to temporarily keep the hair follicles in place while the procedure is being performed.

35. The method of claim 28, wherein the steps of directing the hair follicles comprises combing the hair follicles away from the opening of the frame.

\* \* \* \* \*